United States Patent [19]

Umezawa et al.

[11] 4,318,847
[45] Mar. 9, 1982

[54] PHYSIOLOGICALLY ACTIVE TETRAPEPTIDES

[75] Inventors: Hamao Umezawa, Tokyo; Takaaki Aoyagi, Fujisawa; Tomio Takeuchi, Tokyo; Taiji Inui, Chigasaki, all of Japan

[73] Assignee: Zaidan Hojin Biseibutsu Kagaku Kenkyu Kai, Tokyo, Japan

[21] Appl. No.: 167,586

[22] Filed: Jul. 11, 1980

[30] Foreign Application Priority Data

Jul. 13, 1979 [JP] Japan .................................. 54-89551

[51] Int. Cl.³ .......................................... C07C 103/52
[52] U.S. Cl. ............................................. 260/112.5 R
[58] Field of Search .................................. 260/112.5 R

[56] References Cited

U.S. PATENT DOCUMENTS 4,126,606 11/1978 Umezawa et al. ............ 260/112.5 R

*Primary Examiner*—Delbert R. Phillips
*Attorney, Agent, or Firm*—Herbert W. Taylor, Jr.

[57] ABSTRACT

This invention provides tetrapeptide derivatives of the formula (I):

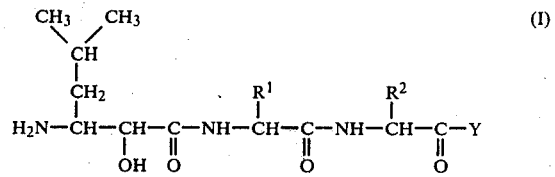

wherein $R^1$ and $R^2$ are methyl, 1-methylethyl, 2-methylpropyl, 1-hydroxyethyl, 2-carboxyethyl or 4-aminobutyl and Y is

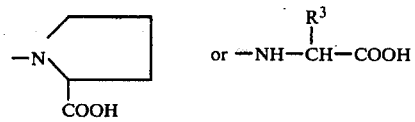

wherein $R^3$ is methyl, 1-methylethyl, 2-methylpropyl, 1-methylpropyl, hydroxymethyl, 1-hydroxyethyl, carboxymethyl, 2-carboxyethyl, 4-aminobutyl, 3-guanidinopropyl, benzyl or p-hydroxybenzyl excluding the compounds in which $R^1$ and $R^2$ are each 1-methylethyl and also $R^3$ is carboxymethyl or 2-carboxyethyl, the first and leftmost β-amino acid moiety in said tetrapeptide derivatives having the (2S,3R)-configuration and a primary amino group and the second, third and fourth α-amino acid moieties in said tetrapeptide derivatives having the L-configuration. These compounds have an inhibitory activity on several types of aminopeptidases.

25 Claims, No Drawings

PHYSIOLOGICALLY ACTIVE TETRAPEPTIDES

BACKGROUND OF THE INVENTION

1. Field of the Invention

This invention relates to synthetic chemical compounds which are tetrapeptides and exhibit inhibitory activity against enzymes such as aminopeptidases.

2. Description of the Prior Art

Several physiologically active peptides or N-acylated peptides have been found in the culture broths by some of the present inventors. These substances, e.g. leupeptin, antipain, chymostatin and pepstatin, inhibit trypsin, papain, chymotrypsin and pepsin, respectively, but all these inhibitors have their effects on proteases which act in endo-type reaction. For further disclosures of these see Enzyme Inhibitors of Microbial Origin, Hamao Umezawa, University of Tokyo Press (1972) in Chapter IV, Inhibitors of Proteolytic Enzymes (pages 15–52) as follows:

| Peptides | Page Number |
| --- | --- |
| Leupeptin | 15 |
| Antipain | 29 |
| Chymostatin | 32 |
| Pepstatin | 34 |

Bestatin, which has also been found in a microbial culture broth, inhibits an exo-type proteolytic enzyme, i.e. aminopeptidase B and leucine aminopeptidase, but it does not have any inhibitory effect on aminopeptidase A [U.S. Pat. No. 4,029,547].

Bestatin has the chemical name [(2S,3R)-3-amino-2-hydroxy-4-phenylbutanoyl]-L-leucine and the following structure

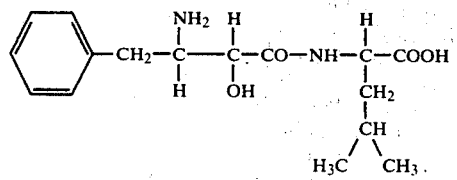

Other peptides were disclosed in U.S. Pat. No. 4,189,604 which claimed compounds having the formula

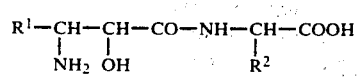

wherein $R^1$ is

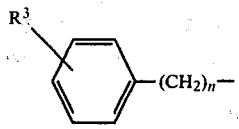

wherein $R^3$ is hydrogen, chloro, methyl, nitro, hydroxy or amino and n is 0 or 1 and $R^2$ is (lower)alkyl having 1 to 6 carbon atoms, hydroxy(lower)alkyl, alkylthioalkyl, carboxamide(lower)alkyl or carboxy(lower)alkyl provided that when $R^1$ is benzyl and $R^2$ is isobutyl the configuration of the compound is (2S,3R2'R), (2S,3S,2'S) or (2S,3S,2'R).

The present authors have discovered that Streptomyces sp. ME98-M3(FERM-P 3722) produces new tetrapeptide compounds of the formula (II) named amastatins which contain at the N-terminal a new β-amino acid unknown in the literature and having the formula

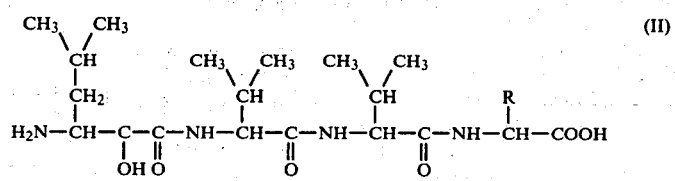

wherein R is a carboxymethyl or 2-carboxyethyl group, and found that these tetrapeptide compounds not only inhibit aminopeptidase A but also stimulate the antibody formation (U.S. Pat. No. 4,167,448; J. Antibiotics 31(6) 636–638, 1978). In the present specification, the said new β-amino acid, 3-amino-2-hydroxy-5-methylhexanoic acid, is abbreviated AHMHA and its residue AHMHA-.

SUMMARY OF THE INVENTION

Using AHMHA as the basic moiety, the present authors have synthesized various peptide derivatives in order to look for new compounds which are more inhibitory than amastatins and have novel physiological activities. As a result, they have discovered that peptide derivatives of the formula (I) are not only inhibitory on the said types of aminopeptidase but also inhibit triaminopeptidase severely as a new physiological effect. Based on these findings, the present invention has been established.

In particular, the present invention concern new tetrapeptide derivatives of the formula (I)

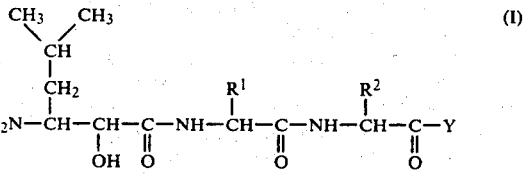

wherein $R^1$ and $R^2$ are methyl, 1-methylethyl, 2-methylpropyl, 1-hydroxyethyl, 2-carboxyethyl or 4-aminobutyl and Y is

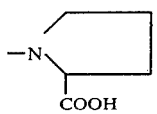 or 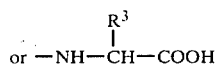

wherein R³ is methyl, 1-methylethyl, 2-methylpropyl, 1-methylpropyl, hydroxymethyl, 1-hydroxyethyl, carboxymethyl, 2-carboxyethyl, 4-aminobutyl, 3-guanidinopropyl, benzyl or p-hydroxybenzyl excluding the compounds in which R¹ and R² are each 1-methylethyl and also R³ is carboxymethyl or 2-carboxyethyl, the first and leftmost β-amino acid moiety in said tetrapeptide derivatives having the (2S,3R)-configuration and a primary amino group and the second, third and fourth α-amino acid moieties in said tetrapeptide derivatives having the L-configuration.

Preferred embodiments of the present invention are the compounds of Formula I in which R¹ is 1-methylethyl and R² is not 1-methylethyl, and preferably in which R² is 4-aminobutyl, 1-hydroxyethyl, 2-methylpropyl or 2-carboxyethyl and especially in which R³ is carboxymethyl.

Other preferred embodiments of the present invention are the compounds of Formula I in which R² is 1-methylethyl and R¹ is not 1-methylethyl and preferably in which R¹ is 4-aminobutyl, 1-hydroxyethyl, 2-methylpropyl or 2-carboxyethyl and especially those in which R³ is carboxymethyl.

Yet other preferred embodiments of the present invention are the compounds of Formula I in which both R¹ and R² are 1-methylethyl and preferably in which R³ is 1-hydroxyethyl,

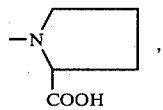

benzyl, 1-methylethyl, 4-aminobutyl or 3-guanidinopropyl.

In the subsequent explanation of the present invention, the following abbreviations of amino acids, peptides and related compounds which accord with the recommendations by the IUPAC-IUB joint committee (Biochemistry 6, 362(1967); Biochemistry 11, 1726(1972)) are employed in the present specification. Other relevant compounds will be explained on first appearance and the corresponding abbreivations in parentheses will be used thereafter.

For amino acids, the abbreivations are given in parenthesis as follows: valine(Val), leucine(Leu), threonine(Thr), aspartic acid(Asp), glutamic acid(Glu), lysine(Lys), arginine(Arg), phenylalanine(Phe) and proline(Pro).

When the linkage position is at the amino terminal, it is shown by drawing the hyphen at the left side of the relevant amino acid. Similarly the linkage at the carboxyl terminal and those at both terminals are presented with the hyphen(s) at the right side and both sides of the amino acid respectively. With glycine as example, they are shown as follows: -Gly, Gly-, -Gly-.

The details of the present invention will be explained with exemplary compounds in the following: as described above, the componds of the formula (II) which are produced by fermentation of Streptomyces sp. ME98-M3(FERM-P 3722) are proved to be inhibitory on aminopeptidase. In addition, those new peptide derivatives of the formula (I) of the present invention are also aminopeptidase-inhibitory and can be obtained by peptide formation of a new β-amino acid, AHMHA, contained in the peptides of the formula (II), with major α-amino acids which are common constituents of protein, such as glycine, valine, leucine, threonine, aspartic acid, glutamic acid, lysine, arginine, phenylalanine, trysoine and proline.

AHMHA, an essential constituent of the peptide derivatives of the present invention, has the particular configuration of (2S,3R) in the natural peptide products of the said actinomycete. As described later, AHMHA can also be obtained in the other configurations by synthetic methods and may be similarly incorporated as a constituent amino acid in the present invention. According to the present invention, however, the peptide compounds of the present invention which are found most suitable are those composed of AHMHA in the (2S,3R) R-configuration and α-amino acids in the L-form.

AHMHA constitutes the N-terminal amino acid of these new peptides. As the second and the third α-amino acid constituents, netural and basic amino acids such as valine, alanine leucine, threonine and lysine are preferable. When the fourth and C-terminal amino acid moiety has a free amino or carboxyl group, the corresponding acid or alkali addition salts may be prepared. It can be basic, neutral or acidic and thus common α-amino acids are employable.

The peptide derivatives of the present invention can be produced from the said amino acids by various known methods of peptide synthesis and most profitably by liquid phase peptide synthesis.

In the following, the methods of preparation of the tetrapeptide derivatives according to the present invention will be explained concretely.

After amastatins are hydrolysed in acidic or alkaline conditions, AHMHA is separated and purified from the hydrolysate by a suitable combination of various chromatographic methods for separation of amino acids. AHMHA thus obtained has the (2S,3R)-configuration.

The above stereoisomer of AHMHA can also be obtained by a method described in Agric. Biol. Chem. 43(3), 591–596(1979). First of all, the amino group of the α-amino acid isomer which has the stereo-configuration corresponding to the final isomer of 3-amino-2-hydroxycarboxylate (for example, D- or L-leucine) is protected with a protecting group conventionally known in the peptide chemistry. The protected amino acid is treated with a secondary amine such as pyrazole to give amide. The amide is reduced to aldehyde with lithium aluminium hydride, for example, in ether at a low temperature below 0° C. The treatment of the aldehyde with sodium bisulfite gives an addition product, which is further allowed to react with cyanate to provide cyanohydrin. The cyanohydrin that corresponds to 3(R or S)-amino-2(R or S)hydroxynitrile protected in the amino group is then converted by hydrolysis to the corresponding 3(R or S)-amino-2(R or S)hydroxycarboxylate.

The mixture of the two diastereomers thus obtained can be resolved into two isomers by chromatography or with an optical resolver. An example of processes for preparation of AHMHA employable in the present invention is illustrated below with experimental results.

The abbreviations of the protecting groups used in the present invention are as follows: benzyloxycarbonyl(Z), t-butoxycarbonyl(Boc), benzyl(Bzl), benzyloxy(OBzl), tosyl(Tos), methoxy(OMe), trityl(Trt).

EXPERIMENT 1

Synthesis of (2S,3R)-AHMHA

1-(1) Synthesis of Z-D-Leu

Benzyloxycarbonyl chloride (abbreviated Z-Cl hereafter) (65 ml) and 114 ml of 4 N NaOH were simultaneously added under agitation with ice-cooling to a solution of 50 g of D-Leu in 191 ml of 2 N NaOH and stirred for a further one hour. After the reaction mixture was diluted with one liter of distilled water, it was rinsed three times with 300 ml each of ethyl acetate. The aqueous layer was adjusted to pH 2.0 with 4 N HCl under cooling with ice. The oily material formed was extracted with ethyl acetate. The ethyl acetate extract, after being washed with a saturated solution of sodium chloride, was dehydrated over anhydrous sodium sulfate and then evaporated under reduced pressure to give 44 g of colorless, transparent syrup.

1-(2) Synthesis of Z-D-Leu-(3,5)dimethylpyrazolide

N,N'-Dicylcohexylcarbodiimide (abbreviated DCCD hereafter) (68.3 g) was put into a solution of 87.8 g of Z-D-Leu in 900 ml of tetrahydrofuran (abbreviated THF hereafter) with ice-cooling and stirred for 20 minutes. After 31.8 g of 3,5-dimethylpryazole was added, the reaction mixture was agitated for 3 hours. The N,N'-dicyclohexylurea (abbreviated DCU hereafter) thus precipitated was removed by filtration. The solvent was evaporated off in vacuo and the residue was taken up in 500 ml of benzene. After insoluble matter was separated by filtration, the filtrate was dehydrated over anhydrous sodium sulfate and then subjected to evaporation under reduced pressure to give pale yellow syrup. Hexane (500 ml) was added to the syrup and was allowed to stand overnight at 5° C. The crystals thus formed were collected by filtration and dried to give 89.6 g of Z-D-Leu-(3,5)-dimethylpyrazolide.

1-(3) Synthesis of Z-D-leucinal

A suspension of 25 g of lithium aluminium hydride in 160 ml of THF was slowly added dropwise at −25° C. to a solution of 43.3 g of Z-D-Leu-(3,5)dimethylpyrazolide in 433 ml of THF over a period of one and a half hours and was stirred for a further 2 hours. After being cooled to −70° C., the reaction mixture was acidified to pH 2 with 3 N hydrochloric acid. The THF solvent was evaporated off at room temperature in vacuo and the remaining hydrochloric acid solution was subjected to extraction twice with 100 ml each of ether and once with 50 ml ether. The ether extracts were combined and then washed once with 20 ml of 1 N hydrochloric acid and three times with 20 ml each of saturated solution of sodium chloride. The dehydration over anhydrous sodium sulfate followed by evaporation under reduced pressure gave 24.7 g of colorless, clear syrup of Z-D-leucinal.

1-(4) Synthesis of (3R)-3-benzyloxycarbonylamino-2-hydroxy-5-methylenantonitrile Z-D-Leucinal (24.7 g) in 50 ml of ethyl acetate was mixed with 22.7 g of sodium hyposulfite in 100 ml of distilled water and agitated for 16 hours. Then 5.35 g of sodium cyanide was added to the solution and it was stirred for 3 hours. The reaction product was extracted three times with 50 ml each of ethyl acetate and the combined ethyl acetate extracts were washed once with 20 ml of distilled water and three times with 30 ml each of saturated solution of sodium chloride. After the organic layer was dehydrated over anhydrous sodium sulfate, the solvent was evaporated off under reduced pressure to provide 22.5 g of syrup. The syrup was charged on a silica gel column (Wakogel 200, a product of Wako Pure Chemical Industries, Ltd.; 125 g) and developed with a mixture of benzene and ethyl acetate (10/1) to yield 18.1 g of syrup of (3R)-3-benzyloxycarbonylamino-2-hydroxy-5-methylenantonitrile.

Rf: 0.29 (benzene/ethyl acetate=10/1, a silica gel 60 F$_{254}$ plate, a product of E. Merck).

n.m.r. δppm (CDCl$_3$): 0.9 (6H, each d, J 5 Hz, —CH(CH$_3$)$_2$), 1.3~1.7 (3H, m, H-4,4, H-5), 3.6~4.2 (1H, m, H-3), 4.4~4.6 (1H, m, H-2),
5.1 (2H, s, —CH$_2$Ph), 5.2~5.5 (1H, m, —NH—), 5.5~5.9 (1H, m, —OH), 7.31 (5H, s, —CH$_2$Ph).

1-(5) Synthesis of (3R)AHMHA

A solution of 18.1 g of (3R)-3-benzyloxycarbonylamino-2-hydroxy-5-methylenantonitrile in a solvent mixture of 163 ml of dioxane and 78 ml of anisole was mixed with 163 ml of concentrated hydrochloric acid and heated under reflux with agitation for 9 hours at a temperature of 115°–120° C. in an oil bath. The reaction solution was condensed to 100 ml under reduced pressure and then subjected to extraction twice with 50 ml each of ethyl acetate. After the solvent was removed from the combined extracts by evaporation in vacuo, the evaporation residue was dissolved in 200 ml of distilled water and evaporated to dryness under reduced pressure. This dissolution and evaporation step was repeated three to four times. The evaporation residue thus obtained was applied on a column of sulfonate-type polystyrene ion exchange resin such as Dowex 50 W×10 (140 ml, 200–400 mesh, a product of Dow Chemical Co.). After washing with 300 ml of distilled water, the column was eluted with 0.3 N ammonia. Ninhydrin-positive eluate fractions were collected and evaporated to dryness under reduced pressure. Recrystallization of the solid matter from a solvent mixture of 100 ml of hot water and 200 ml of isopropyl alcohol gave 6.9 g of (3R)AHMHA.

Rf: 0.33 (butanol/acetic acid/water=4/1/1, a silica gel plate as described above).

1-(6) Isolation of (2S,3R)AHMHA

Twenty grams of cellulose powder was well mixed with a solution of 2.0 g of (3R)-AHMHA crystals in 100 ml of distilled water and then evaporated to dryness under reduced pressure to give AHMHA-cellulose powder. The AHMHA-cellulose powder was placed on top of a column of cellulose powder (1.8 liters) which had been packed with a developing solvent system of ethyl acetate/acetic acid/pyridine/water=5/1/1/1 (upper layer). The column elution with the said solvent system separated 750 mg of (2S,3R)AHMHA from its diastereomer mixtures.

(2S,3R)AHMHA

Rf: 0.31 (the above-described developing solvent system, a cellulose thin-layer plate from Funakoshi Pharmaceutical Co., Ltd.).

m.p.: 231°–232° C.

$[\alpha]_D^{23}$: −28.4° (c=0.5, CH$_3$COOH).

(2R,3R)AHMHA

Rf: 0.27 (under the same conditions as described above).

m.p.: 230°–231° C.

$[\alpha]_D^{23}$: +28.1° (c=0.5, $CH_3COOH$).

1-(7) Synthesis of Z-(2S,3R)AHMHA.

(2S,3R)AHMHA(123.2 mg) and 192.6 mg of sodium bicarbonate were suspended in 3.6 ml of a solvent mixture of THF/distilled water (1/1). Z-Cl (0.16 ml) was added drop by drop to the suspension under cooling with ice and then stirred for 8 hours. After THF was evaporated off under reduced pressure, the remaining alkaline aqueous solution was diluted with 10 ml of distilled water and was rinsed twice with 2 ml each of hexane and once with 2 ml of ethyl acetate. The acidification of the aqueous solution to pH 2 with 6 N hydrochloric acid produced oil which was extracted four times with 3 ml each of ethyl acetate. The organic extracts were pooled and washed twice with 2 ml each of saturated solution of sodium chloride. The dehydration with anhydrous sodium sulfate and the subsequent removal of the solvent under reduced pressure yielded 154.4 mg of dry syrup of Z-(2S,3R)AHMHA from which 120 mg of Z-(2S,3R)-AHMHA crystals were obtained by recrystallization from a solvent mixture of ether and hexane.

n.m.r. δppm ($CDCl_3$): 0.9 (6H, d, $J_{5,6}$5Hz, —CH($CH_3$)$_2$), 1.2~1.8 (3H, m, H-4,4′, H-5), 3.9~4.5 (2H, m, H-2, H-3), 5.83 (2H, s, —$CH_2$Ph), 5.2~5.8 (2H, m, —OH, —NH—).

m.p.: 85°~87° C.

IR: νmax/KBr $cm^{-1}$: 1705(carboxyl C=O), 1640(urethane C=O), 3310(urethane—NH—), 3520(—OH).

1-(8) Synthesis of Z-(2S,3R)AHMHA(OZ).

Using 300 mg of (2S,3R)AHMHA and 783 mg of $NaHCO_3$, the same procedure as detailed in 1-(7) was performed to provide 254 mg of syrup of Z-(2S,3R)AHMHA(OZ).

Rf: 0.4(benzene/ethyl acetate/isopropyl alcohol=30/20/5, a silica gel plate as described above).

n.m.r. δppm ($CDCl_3$): 0.9 (6H, d, $J_{5,6}$5Hz, —CH($CH_3$)$_2$), 1.2~1.8 (3H, m, H-4,4′, H-5), 4.15~4.75 (1H, m, H-3), 4.95 (1H, d, J 2.5 Hz, H-2), 5.05 (2H, s, —$CH_2$Ph). 5.15 (2H, s, —$CH_2$Ph), 7.26 (5H, s, —$CH_2$Ph), 7.31 (5H, s, —$CH_2$Ph), 8.0~9.2 (2H, m, —NH—, —COOH).

For preparation of tetrapeptide derivatives of the formula (I) from AHMHA and other constituent amino acids such as L-Val and amino acid Y in the formula (I), the conventional liquid phase peptide synthesis is most favorable. In brief, for production of peptide derivatives of the present invention, the α-amino or carboxyl group of any one constituent amino acid in the formula (I) may be linked sequentially to the neighboring amino acid or peptide by peptide bond formation until the desired length of the peptide can be obtained. In practice it seems to be advantageous that the dipeptide containing constituent amino acid Y of the formula (I) is first synthesized and then sequentially elongated to tetrapeptides. For this purpose, the amino and carboxyl groups of amino acid are usually protected as follows: after functional groups other than the α-amino group of amino acid Y of the formula (I) (for example, carboxyl, hydroxyl, amino and thiol groups) are appropriately protected, the amino group of L-valine is covered with a suitable protecting radical which can be cleaved off without affecting the protected functional groups of amino acid Y. These two protected amino acids are linked together to give the dipeptide by means of conventional methods for peptide formation. For example, the carbodiimide method using DCCD, the mixed-acid anhydride method with chloroformic esters, the azide method due to azidation of the carboxyl group, the active ester method by virtue of ester formation with N-hydroxysuccinimide, etc. are profitably employable. For connection of the next amino acid similarly protected, only the α-amino-protecting group is cleaved off from the L-valine moiety of the dipeptide by an appropriate method (for example, catalytic reduction, treatment with trifluoroacetic acid (TFA), processing with hydrobromide in acetic acid or with metallic sodium in liquid ammonia, saponification with an alkali, treatment with anhydrous hydrofluoric acid, etc.) under preliminarily chosen reaction conditions where the other protecting groups easily survive. (Although any type of the protecting group will do at the final stage of peptide formation, it is favorable to employ such a combination of protecting groups that all of them can be simultaneously cleaved off under the same treatment conditions at the termination of synthesis.) After the same procedure of peptide elongation by one amino acid unit and removal of the relevant protecting group is repeated until the desired length of the peptide is obtained, the remaining protecting groups are finally cleaved off to give the peptide derivative of the present invention.

Tetrapeptide derivatives of the present invention prepared as described above markedly inhibit aminopeptidase A (abbreviated AP-A hereafter), aminopeptidase B (abbreviated AP-B hereafter), leucine aminopeptidase (abbreviated Leu-AP hereafter), glycylprolylleucine tripeptidylaminopeptidase (abbreviated Gly-Pro-Leu-AP hereafter) and glycylhistidyllysine tripeptidylaminopeptidase (abbreviated Gly-His-Lys-AP hereafter). In the following, the assay methods of enzyme activity will be described for the above enzymes:

(1) AP-A(E.C. 3,4,11,7)

The activity of this enzyme was assayed by a modification of the method of Nagatsu et al. (I. Nagatsu, T. Nagatsu, T. Yamamoto and G. G. Glenner: BIOCHIMICA ET BIOPHYSICA ACTA 198, 255–270(1970)). That is, 0.25 ml of 2 mM L-α-glutamyl-β-naphthylamide, 0.54 ml of 0.1 M Tris-HCl buffer, pH 7.0, 0.01 ml of 0.1 M calcium chloride and 0.1 ml of a test sample in water were mixed and kept at 37° C. for 3 minutes. The reaction was initiated by addition of 0.1 ml of an AP-A solution which was obtained by ammonium sulfate fractionation according to the method of Nagatsu et al. After incubation at 37° C. for 30 minutes, 1 ml of 1.0 M acetate buffer, pH 4.2, containing 1.0 mg/ml Garnet GBC (orthoaminoazotoluene diazonium salt) and 10% Tween 20 (Atlas Chemical Co., U.S.A.) was added to the reaction solution and then allowed to stand at room temperature for 15 minutes. The absorbance of the test solution (a) was measured at 530 nm. The control solution without the test sample was used as the blank test (absorbance (b)). The inhibition percentage on aminopeptidase A was calculated as [(b-a)/b]×100.

(2) AP-B(E.C. 3,4,11,6)

For activity measurement, the method of Hopsu et al. (V. K. Hopsu, K. K. Makinen and G. G. Glenner: ARCHIVES OF BIOCHEMISTRY AND BIOPHYSICS 114, 557(1966)) was modified. Namely, a reaction mixture containing 0.25 ml of 2 mM L-α-arginyl-β-naphthylamide, 0.63 ml of 0.1 M Tris-HCl buffer, pH 7.0, and 0.1 ml of an aqueous solution of a test sample was maintained at 37° C. for 3 minutes. The enzyme reaction was started by addition of 0.02 ml of an AP-B solution that was purified from the rat liver by the method of Hopsu et al. using Sephadex G-100 (cross-linked dextran gel, a product of Pharmacia Fine Chemicals AB, Sweden). After 30 minutes of reaction at 37° C., the inhibition percentage was obtained as described in (1).

(3) Leu-AP(E.C. 3,4,11,1)

For enzyme assay, 0.25 ml of 2 mM L-α-leucyl-β-naphthylamide, 0.6 ml of 0.1 M Tris-HCl buffer, pH 7.6, and 0.1 ml of an aqueous solution containing a test compound were mixed and allowed to stand at 37° C. for 3 minutes. After a 20-fold dilution of Leu-AP (Boehringer-Mannheim Co.) in 0.1 M Tris-HCl buffer, pH 7.6 (0.05 ml) was added to the solution, the reaction was performed at 37° C. for 30 minutes. The inhibition percentage was measured as detailed in (1).

(4) Gly-Pro-Leu-AP

According to the method of Aoyagi et al. (T. Aoyagi et al: BIOCHIMICA ET BIOPHYSICA ACTA 452, 131–143(1976)), after a reaction mixture consisting of 0.25 ml of 2 mM glycyl-L-α-prolyl-L-α-leucyl-β-naphthylamide (Buchem Fine Chemicals Co.), 0.6 ml of the Hanks solution, pH 7.2, and 0.1 ml of an aqueous test solution was kept at 37° C. for 3 minutes, 0.05 ml of a Gly-Pro-Leu-AP that was purified from the cell membrane fraction of the rat liver was added and the reaction was carried out at 37° C. for 30 minutes. The same procedure as described in (1) was used for calculation of the inhibition percentage.

The Hanks solution listed above was prepared by dissolving 8.0 g sodium chloride, 0.4 g potassium chloride, 0.14 g calcium chloride, 0.10 g magnesium chloride, 0.06 g disodium-monohydrogen phosphate, 0.06 g monopotassium dihydrogen phosphate, 0.10 g magnesium sulfate and 1.0 g glucose in 1 liter of distilled water and adjusting the solution to pH 7.2 with solid sodium bicarbonate (about 350 mg).

(5) Gly-His-Lys-AP

For enzyme assay, 0.25 ml of 0.5 mM glycyl-L-α-histidyl-L-α-lysyl-β-naphthylamide, 0.62 ml of the Hanks solution, pH 7.2, and 0.1 ml of an aqueous solution of a substance to be tested were combined and maintained at 37° C. for 3 minutes. Gly-His-Lys-AP solution (0.03 ml) which was purified from the FM3A cells (a line of culture cells derived from mouse mammary tumor) by the method described in the reference of (4) was added to the solution and incubated at 37° C. for 30 minutes. The inhibition percentage was calculated as shown in (1).

Gly-His-Lys -β-naphthylamide used above was prepared as follows: to a solution containing 1 g of Gly-His-Lys-acetate (Buchem Fine Chemicals Co.) and 3.0 g of sodium bicarbonate in 60 ml of distilled water, 2.13 ml of Z-Cl was added dropwise under cooling with ice and then stirred for 3 hours. The same treatment as detailed above in Experiment 1-(7) was performed to give 605.8 mg of the Z-derivative of the tripeptide. This Z-derivative of the tripeptide and 117 mg of β-naphthylamine were condensed as described in Experiment (1-(2) to yield 600 mg of a solid material. The solid material was dissolved in 10 ml of a solvent mixture of acetic acid and water (1/1) and then shaken overnight together with 30 mg of palladium-carbon in the presence of hydrogen (4 atmospheres). The removal of the catalyst followed by evaporation of the solvent under reduced pressure provided 200 mg of Gly-His-Lys-β-naphthylamide.

n.m.r δppm (CD$_3$OD):

1.4~2.3 (6H, m, —NH—C$\underline{H}$—(C$\underline{H}_2$)$_3$—)

2.9~3.2 (4H, m, —CH$_2$—C$\underline{H}_2$—NH$_2$, $>$CH—C$\underline{H}_2$—C=C$\underline{H}$)

3.7~3.9 (2H, m, NH$_2$—C$\underline{H}_2$—CO—), 6.9~8.3 (9H, m, aromatic).

m.p.: 115°~116° C. (3HCl salt).

[α]$_d^{23}$ −17.5° (C=0.1, H$_2$O) (3HCl salt).

Table 1 summarizes the inhibitory activity of the new tetrapeptide derivatives of the present invention and related peptides on the above-listed enzymes.

TABLE 1

| Peptide | Inhibition rate Enzyme | AP—A | AP—B | Leu—AP | IC/50[1] Gly—Pro—Leu—AP | Gly—His—Lys—AP |
|---|---|---|---|---|---|---|
| X—Val—Val—Asp[2] | | 0.5 | >250 | 0.5 | 0.04 | 0.3 |
| X—Val—Lys—Asp | | 10 | >250 | 3.5 | 1.0 | 1.4 |
| X—Val—Thr—Asp | | 1.0 | >250 | 1.0 | 0.87 | 2 |
| X—Val—Leu—Asp | | 0.3 | >250 | 0.7 | 0.2 | 0.16 |
| X—Val—Glu—Asp | | 8.0 | >250 | 0.1 | 15 | 100 |
| X—Thr—Val—Asp | | 0.15 | >250 | 2.5 | 0.2 | 1.0 |
| X—Leu—Val—Asp | | 5.0 | >250 | 0.3 | 2.5 | 0.8 |
| X—Lys—Val—Asp | | 1.5 | >250 | 110 | 0.25 | 0.4 |
| X—Glu—Val—Asp | | 2 | >250 | 40 | 6 | 2.0 |
| X—Val—Thr—Phe | | 0.6 | >100 | 0.37 | 0.035 | 0.08 |
| X—Lys—Val—Val | | 1.9 | >100 | 180.0 | 0.01 | 0.08 |
| X—Val—Val—Thr | | 2.7 | >250 | 3.5 | 0.1 | 1.5 |
| X—Val—Val—Pro | | 35 | >250 | 2.7 | 0.06 | 0.06 |
| X—Val—Val—Phe | | 7.2 | >250 | 2.2 | 0.05 | 1.1 |
| X—Val—Val—Val | | 4.3 | >250 | 1.8 | 0.04 | 0.91 |
| X—Val—Val—Lys | | 21 | >250 | 32 | 0.4 | 18.5 |
| X—Val—Val—Arg | | 13.5 | >250 | 20 | 0.1 | 18 |
| X—Val—Val—Glu | | 2.0 | >250 | 2.2 | 0.1 | 0.7 |

TABLE 1-continued

| Peptide | Inhibition rate Enzyme | IC/50[1] | | | | |
|---|---|---|---|---|---|---|
| | | AP—A | AP—B | Leu—AP | Gly—Pro—Leu—AP | Gly—His—Lys—AP |
| X—Ala—Ala—Asp | | >250 | >250 | >250 | >100 | >100 |
| X—Val—Val—Val—Asp | | 18 | >250 | 4.2 | 0.04 | 0.1 |
| (2R,3R)X—Val—Val—Asp | | 85 | >250 | >250 | 35 | 82 |
| (2S,3S)X—Val—Val—Asp | | 5.0 | >250 | 5.0 | 0.6 | 2 |
| (2R,3S)X—Val—Val—Asp | | 25 | >250 | 21 | 6.0 | 20 |
| X—Val—Asp | | 12 | >250 | 0.3 | 7.2 | 14 |
| X—Val—Val | | 3.6 | >250 | 0.9 | 0.2 | 11.5 |
| X—Asp | | >250 | >250 | 29 | >100 | >100 |
| X—Val | | 225 | 27 | 0.5 | 12 | 6.7 |
| X—Pro | | 200 | >250 | 21.5 | 8.6 | 56 |

[1]IC/50 (μg/ml) : amount of the peptide to inhibit the intact activity of the target enzyme by 50%.
[2]In the natural type of amastatins, X is 3-amino-2-hydroxy-5-methylhexanoyl(AHMHA—) having the (2S,3R)-configuration. Unless specified otherwise, X has the same meaning as described above hereinafter.

It is quite obvious from Table 1 that the peptide compounds of the present invention have a strong inhibitory activity on the tripeptidylaminopeptidases (Gly-Pro-Leu-AP and Gly-His-Lys-AP).

Shlesinger et al have recently isolated Gly-His-Lys as a tumor cell growth-promoting tripeptide, which seems to be produced by vivo by tripeptidase (EXPERIENTIA 32, 324–325 (1977)).

Therefore it can be expected that suppressive effects on growth of mammalian tumor cells will be obtained by administration of amastatins and tetrapeptide derivatives of the present invention.

Thus the present invention provides new peptide derivatives that exhibit inhibitory activity on aminopeptidase and tripeptidylaminopeptidase in vitro and in vivo and that can be expected to be effective as an antitumor agent.

DESCRIPTION OF THE PREFERRED EMBODIMENTS

Example 1

Synthesis of (2S,3R)-AHMHA-Val-Lys-Asp 1-(1) Synthesis of Boc-Lys(Z)-Asp(OBzl)$_2$ DCCD (612 mg) was mixed with a suspension of 1.03 g of Boc-Lys(Z), 1.31 g of Asp(OBzl)$_2$·TosOH and 437 mg of HOBt in anhydrous tetrahydrofuran (abbreviated THF hereafter) and stirred for 5 minutes. Then 0.414 ml of anhydrous triethylamine was added dropwise to the suspension and agitated for 8 hours. After DCU formed was removed by filtration, the evaporation of the solvent from the filtrate under reduced pressure yielded 4.8 g of syrup. This syrup was purified by silica gel column chromatography (Wakogel C-200, 50 g; Wako Pure Chemical Industries, Ltd.) using a solvent system of benzene and ethyl acetate (5/1) to give 1.74 g of crystals of the title compound.

Rf: 0.12 (benzene/ethyl acetate=5/1; a Silica gel 60 F$_{254}$ plate, E. Merck).

m.p.: 106°~107.5° C.

$[\alpha]_D^{22}$: −12.4° (c=2.0, CH$_3$OH).

n.m.r δppm (CDCl3): 1.3~1.9 (6H, m, —(C$\underline{H}_2$)$_3$—), 1.44 (9H, s, —C(C$\underline{H}_3$)$_3$), 2.9~3.4 (4H, m, —C$\underline{H}_2$CO—, —C$\underline{H}_2$NH—), 4.7~5.2 (2H, m, —C$\underline{H}$NH— × 2)

5.05 (2H, s, —C$\underline{H}_2$Ph), 5.11 (4H, s, —C$\underline{H}_2$Ph×2), 6.8~7.2 (2H, m, —N$\underline{H}$—×2), 7.34 (15H, s, —CH$_2$P$\underline{h}$×3). (Ph means the phenyl group.)

IR: νmax/KBr cm$^{-1}$: 3325(—N$\underline{H}$CO—), 1735 (ester C=O), 1690 (urethane C=O), 1650 (amide C=O).

1-(2) Synthesis of Boc-Val-Lys(Z)-Asp(OBzl)$_2$

Trifluoroacetic acid (0.6 ml) was added dropwise to a solution of 1.14 g of Boc-Lys(Z)-Asp(OBz) in 11 ml of methylene chloride under cooling with ice and then warmed to room temperature. Three hours later, the solvent was evaporated off. The evaporation residue was dissolved in 20 ml of ethyl acetate and washed three times with 5 ml each of cold saturated solution of sodium bicarbonate and then twice with 5 ml each of saturated solution of sodium chloride. After dehydration over anhydrous sodium sulfate, the removal of the solvent by evaporation in vacuo provided 873 mg of free amine. This free amine (873 mg), 314 mg of Boc-Val and 234 mg of 1-hydroxybenzotriazole (abbreviated HOBt hereafter) were dissolved in 17 ml of anhydrous THF. After 328 mg of DCCD was added under ice-cooling, the mixture was stirred for 4 hours at room temperature. DCU formed was filtered off and the filtrate was evaporated to dryness under reduced pressure. The evaporation residue was chromatographed on a silica gel column (40 g, same supporting material as described above) using a developing solvent mixture of benzene, ethyl acetate and chloroform (2/1/1) to yield 906 mg of crystals of Boc-Val-Lys(Z)-Asp(OBzl)$_2$.

Rf: 0.54 (benzene/ethyl acetate/chloroform=1/1/1, a silica gel plate as described above).

n.m.r δppm (CDCl$_3$):

| 0.8 and 0.91 | (6H, each d, J = 4Hz, —CH$\overset{\text{CH}_3}{\underset{\text{CH}_3}{<}}$) |
|---|---|
| 1.39 | (9H, s, —C(C$\underline{H}_3$)$_3$) |
| 1.3~2.2 | (7H, m, —(CH$_2$)$_3$—, —C$\underline{H}$$\overset{\text{CH}_3}{\underset{\text{CH}_3}{<}}$) |
| 2.8~3.4 | (4H, m, —C$\underline{H}_2$NH—, C$\underline{H}_2$—C(=O)—) |
| 3.8~4.1 | (1H, m, —NH—C$\underline{H}$—C(=O)—) |
| 4.2~4.7 | (1H, m, —NH—C$\underline{H}$—C(=O)—) |
| 4.8~5.1 | (1H, m, —NH—C$\underline{H}$—C(=O)—) |

5.02 and 5.08 (6H, each s, —C$\underline{H}_2$Ph×3), 5.0~5.5 (2H, m, —N$\underline{H}$—×2), 6.8~7.0 (2H, m, —N$\underline{H}$—×2), 7.26 and 7.30 (15H, each s, —CH$_2$P$\underline{h}$×3).

m.p: 138°~139° C.

$[\alpha]_D^{22}$: −23.1° (c=1.52, CH$_3$OH).

IR: νmax/KBr cm⁻¹: 3325(—NH—CO—), 1740, 1730 (ester C=O), 1690 (urethane C=O), 1645 (amide C=O).

1-(3) Synthesis of Z-(2S,3R)-AHMHA-Val-Lys(Z)-Asp(OBzl)₂

One milliliter of trifluoroacetic acid was added dropwise to a solution of 503 mg of Boc-Val-Lys-Asp(OBzl)₂ in 4 ml of methylene chloride under cooling with ice and allowed to stand for 2 hours at room temperature. After the solvent was evaporated off in vacuo, the evaporation residue was dissolved in 20 ml of ethyl acetate. The ethyl acetate solution was washed three times with 2 ml each of cold saturated solution of sodium bicarbonate and then twice with 2 ml each of saturated solution of sodium chloride. After dehydration over anhydrous sodium sulfate, the solvent was removed by evaporation under reduced pressure to provide 350 mg of free amine. This free amine, 157 mg of Z-(2S,3R)-AHMHA(Z) and 107 mg of HOBt were dissolved in 13 ml of anhydrous THF. Under cooling with ice, 150 mg of DCCD was added to the mixture and stirred for 5 hours. DCU formed was removed by filtration and the solvent was evaporated off in vacuo to give 502 mg of solid matter. Silica gel column chromatography (20 g silica gel; same supporting material as described above) using a solvent mixture of benzene, chloroform and acetone (1/1/1) yielded 387 mg of Z-(2S,3R)-AHMHA(Z)-Val-Lys(Z)-Asp(OBzl)₂ in the crystalline form.

Rf: 0.57 (benzene/chloroform/acetone=1/1/1, a silica gel plate as described above).

m.p: 162°~163° C.

$[\alpha]_D^{22}$: −18.0° (c=0.88, CH₃OH).

n.m.r δppm (CDCl₃): 0.8~0.95 (12H, m, —CH(CH₃)₂×2), 1.2~1.8 (10H, m, —(CH₂)—×3, —CH(CH₃)₂×2, —CH₂—(CH(CH₃)₂), 2.8~3.2 (4H, m, —CH₂NH—, —CH₂CO—), 3.8~4.25

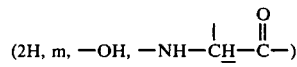
(2H, m, —OH, —NH—CH—C—)

(4.25~4.6 (2H, m, N—CH—CO×2), 4.8~5.1 (1H, m, N—CH—CO), 5.03, 5.06, 5.11, 5.12 (8H, each s, CH₂Ph×4), 7.35 (20H, s, CH₂Ph×4).

IR: ν$_{max}$$^{KBr}$ cm⁻¹: 3325 (—NH—CO—), 1750, 1735 (ester C=O), 1695 (urethane C=O), 1645 (amide C=O).

1-(4) Synthesis of (2S,3R)-AHMHA-Val-Lys-Asp

Z-(2S,3R)-AHMHA-Val-Lys(Z)-Asp(OBzl)₂ (372 mg) was dissolved in 13 ml of a solvent mixture of acetic acid, dioxane and distilled water (mixing ratio 11/2/1) and then shaken for 3 hours in the presence of 38 mg of 10% palladium-carbon catalyst in the atmosphere of hydrogen at 3.5 kg/cm². After the palladium-carbon catalyst was removed by filtration, the solvent was evaporated off under reduced pressure. The evaporation residue was dissolved in 10 ml of distilled water and the evaporation followed by dissolution in water was repeated 3-4 times. Recrystallization in a solvent mixture of 5 ml of distilled water and 10 ml of isopropyl alcohol provided 152 mg of (2S,3R)-AHMHA-Val-Lys-Asp.

Rf: 0.22 (butanol/acetic acid/water=4/1/2, a silica gel plate as described above).

m.p.: 240°-260° C. under decomposition.

$[\alpha]_D^{22}$: −29.9° (c=2.0, CH₃COOH).

Elemental analysis (for C₂₂H₄₁N₅O₈): Found: C, 52.40%; H, 8.56%; N, 13.58%. Calculated: C, 52.47%; H, 8.21%; N, 13.91%.

Example 2

Synthesis of (2S,3R)-AHMHA-Val-Thr-Asp 2-(1) Synthesis of Boc-Thr(Bzl)-Asp(OBzl)₂

The procedure described in Example 1-(1) was followed with 1.00 g of Boc-Thr(Bzl) and 1.57 g of Asp-(OBzl)₂ to give 1.69 g of crystals of Boc-Thr(Bzl)-Asp(OBzl)₂.

Rf: 0.55 (benzene/ethyl acetate=5/1, a silica gel plate as described above).

m.p.: 75.5°~76.5° C.

$[\alpha]_D^{22}$: +2.25° (c=1.0, CH₃OH).

n.m.r. δppm (CDCl₃):

1.15  (3H, d, J6Hz, >CH—CH₃)

1.45  (9H, s, —C(CH₃)₃)
2.92  (2H, dd, J3.5Hz, 5Hz, CH—CH₂CO—)

3.8~4.4  (2H, m, >CH—OCH₂Ph, >CH—NH—C—O—)

4.52, 4.98 and  (6H, each s, —CH₂—Ph × 3)
5.11
4.85  (1H, —HN—CH<CH₂ )

5.45 (1H, m, —NH—), 7.3.(15H, s, CH₂Ph×3), 7.4~7.6 (1H, m, —NH—).

IR: ν$_{max}$$^{KBr}$ cm⁻¹: 3340 (NH—CO—), 1745, 1735 (ester C=O), 1700 (urethane C=O), 1650 (amide C=O).

2-(2) Synthesis of Boc-Val-Thr(Bzl)-Asp(OBzl)₂

As detailed in Example 1-(2), 1.59 g of Boc-Thr(Bzl)-Asp(OBzl)₂ was treated with trifluoroacetic acid and then condensed with 569 mg of Boc-Val to yield 1.64 g of crystals of Boc-Val-Thr(Bzl)-Asp(OBzl)₂.

Rf: 0.38 (benzene/ethyl acetate=5/1, a silica gel plate as described above).

m.p.: 124.5°~125.5° C.

$[\alpha]_D^{22}$: −7.75° (c=2.0, CH₃OH).

n.m.r. δppm (CDCl₃): 0.9, 0.96, 1.11

(9H, each d, J6Hz, CH(CH₃)₂—CH—CH₃ with OBzl)

1.9~2.3 (1H, m, —CH(CH₃)₂), 2.9 (2H, dd, —CH₂—CO), 3.8~4.4

(3H, m, —HN—CH—C— × 2, —CH—CH₃ with OBzl)

4.55, 4.96, 5.09 (6H, each s, —CH₂Ph×3), 4.8~5.1

(1H, m, N—CH—C—)

7.28 (15H, s, —CH₂Ph×3), 6.8~7.8 (3H, m, —NH—×3)

IR: ν$_{max}$$^{KBr}$ cm⁻¹: 3300 (NH—CO—), 1735 (ester C=O), 1690 (urethane C=O), 1650 (amide C=O).

2-(3) Synthesis of Z-(2S,3R)-AHMHA-Val-Thr(Bzl)-Asp(OBzl)₂

As detailed in Example 1-(3), 676.5 mg of Boc-Val-Thr(Bzl)-Asp(OBzl)₂ was treated with trifluoroacetic acid and then condensed with 283 mg of (2S,3R)-AHMHA to yield 555 mg of the title compound.

Rf: 0.58 (benzene/ethyl acetate=1/1, a silica gel plate as described above).
m.p.: 126°~127.5° C.
$[\alpha]_D^{22}$: −5.91° (c=2.0, CH₃OH).
n.m.r. δppm (CDCl₃): 0.88, 0.91, 1.10

(15H, each d, J6Hz, —CH(CH₃)₂ × 2, —CH—CH₃)

1.2~2.1 (4H, m, —CH(CH₃)₂×2, —CH₂—CH(CH₃)₂),
2.9 (2H, dd, —CH₂—CO), 3.8~4.5

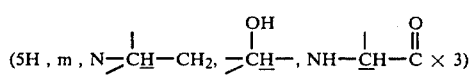

(5H, m, N⁻CH—CH₂, ⁻CH—, NH—CH—C × 3)

4.55, 4.98, 5.05, 5.08 (2H, s, —CH₂Ph×4), 4.8~5.2

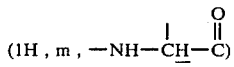

(1H, m, —NH—CH—C)

4.5~4.7 (1H, m, —OH), 5.4~5.8 (2H, m, NH×2), 6.8~7.1 (1H, m, —NH), 7.5~7.8 (1H, m, —NH), 7.3 (20H, s, CH₂Ph×4).

IR: $\nu_{max}^{KBr}$ cm⁻¹: 3300 (NH—CO—), 1740 (ester C=O), 1690 (urethane C=O), 1650 (amide C=O).

2-(4) Synthesis of (2S,3R)-AHMHA-Val-Thr-Asp

Z-(2S,3R)-AHMHA-Val-Thr(Bzl)-Asp(OBzl)₂ (468 mg) was dissolved in 3.0 ml of a solvent mixture of acetic acid, dioxane and distilled water (mixing ratio 11/2/1) and then shaken with 46 mg of 10% palladium-carbon catalyst in the atmosphere of hydrogen at 3.6 kg/cm² for 26 hours. After the catalyst was filtered off, the filtrate was evaporated to dryness. The evaporation residue was dissolved in 10 ml of distilled water and again evaporated to dryness. Complete removal of the organic solvents by repeating the above evaporation procedure 3-4 times provided 250 mg of the title compound.

Rf: 0.37 (butanol/acetic acid/water=4/1/1, a silica gel plate as described above).
m.p.: 196°-198° C. (transformation into needle crystals around 166°-168° C.).
$[\alpha]_D^{22}$: −19.9° (c=2.0, CH₃COOH).
Elemental analysis (for C₂₀H₃₆N₄O₉): Found: C, 50.18%; H, 7.86%; N, 11.43%. Calculated: C, 50.41%; H, 7.62%; N, 11.76%.

Example 3

Synthesis of (2S,3R)-AHMHA-Val-Leu-Asp

3-(1) Synthesis of Boc-Leu-Asp(OBzl)₂

By the same procedure as presented in Example 1-(1), 1.04 g of Boc-Leu and 2.19 g of Asp(OBzl)₂·TosOH were condensed and then subjected to silica gel column (50 g, same supporting material as described above) chromatography using a developing solvent of benzene and ethyl acetate (mixing ratio 10/1) to yield 2.39 g of syrup of the title compound.

Rf: 0.49 (benzene/ethyl acetate=5/1, a silica gel plate as described above).
$[\alpha]_D^{22}$: −30.7° (c=2.0, CH₃OH).
n.m.r. δppm (CDCl₃): 0.88 (6H, d, J5 Hz, —CH(CH₃)₂), 1.40 (9H, s, —C(CH₃)₃), 1.2~1.7 (3H, m, —CH₂—, —CH(CH₃)₂),

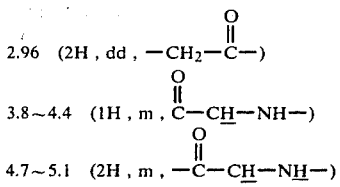

2.96 (2H, dd, —CH₂—C—)

3.8~4.4 (1H, m, C—CH—NH—)

4.7~5.1 (2H, m, —C—CH—NH—)

5.06, 5.13 (4H, each s, CH₂Ph×2), 6.8~7.2 (1H, m, NH), 7.33 (10H, s, CH₂Ph×2).

IR: $\nu_{max}^{KBr}$ cm⁻¹: 3350 (—NH—CO—), 1740 (ester C=O), 1690 (urethane C=O), 1670 (amide C=O).

3-(2) Synthesis of Boc-Val-Leu-Asp(OBzl)₂

By the same procedure as presented in Example 1-(2), 1.80 g of Boc-Leu-Asp(OBzl)₂ was treated with trifluoroacetic acid; condensed with 651 mg of Boc-Val and then submitted to silica gel column (50 g, same supporting material as described above) chromatography employing a solvent mixture of benzene and ethyl acetate (mixing ratio 5/1) to give 1.53 g of crystals of the title compound.

Rf: 0.22 (benzene/ethyl acetate=5/1, a silica gel plate as described above).
m.p.: 112°~113° C.
$[\alpha]_D^{22}$: −39.8° (c=1.57, CH₃OH).
n.m.r. δppm (CDCl₃): 0.8~0.95 (12H, m, —CH(CH₃)₂×2), 1.41 (9H, s, —C(CH₃)₃), 1.3~2.1 (4H, m, —CH(CH₃)₂×2, —CH₂—CH(CH₃)₂), 2.94 (2H, t, —CH₂—CO—),

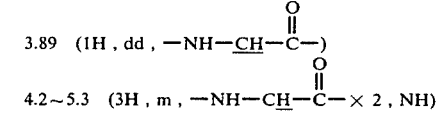

3.89 (1H, dd, —NH—CH—C—)

4.2~5.3 (3H, m, —NH—CH—C—× 2, NH)

5.05, 5.10 (4H, each s, —CH₂—Ph×2), 7.30 (10H, s, —CH₂Ph×2), 6.6 (1H, m, —NH—), 7.08 (1H, m, —NH—).

IR: $\nu_{max}^{KBr}$ cm⁻¹: 3340 (—NH—CO—), 1750 (ester C=O), 1695 (urethane C=O), 1650 (amide C=O).

3-(3) Synthesis of Z-(2S,3R)-AHMHA-Val-Leu-Asp(OBzl)₂

By the same procedure as presented in Example 1-(3), 700 mg of Boc-Val-Leu-Asp(OBzl)₂ was treated with trifluoroacetic acid; condensed with 281 mg of Z-(2S,3R)-AHMHA and recrystallized from a mixture of ethyl acetate and hexane to provide 417 mg of crystals of the title compound.

Rf: 0.60 (benzene/ethyl acetate=1/1, a silica gel plate as described above).
m.p.: 156°~157° C.
$[\alpha]_D^{22}$: −34.1° (c=2.0, CH₃OH).
n.m.r. δppm (CDCl₃): 0.8~1.0 (18H, m, —CH(CH₃)₂×3), 1.3~2.3 (7H, m, —CH₂—CH(CH₃)₂×2, —CH—(CH₃)₂), 2.9 (2H, m, —CH₂—CO—),

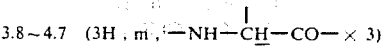

3.8~4.7 (3H, m, —NH—CH—CO— × 3)

4.7~5.3 (1H, m, —NH—C<u>H</u>—CO—)

5.02 (4H, s, —C<u>H</u>₂—Ph×2), 5.06 (2H, s, —C<u>H</u>₂—Ph), 5.5~5.9 (1H, m, —NH), 7.0~7.6 (3H, m, —NH×3), 7.3 (15H, s, —CH₂—P<u>h</u>×3).

IR: ν$_{max}^{KBr}$ cm⁻¹:

$$3325(-\underline{NH}-\overset{O}{\underset{\|}{C}}-),$$

1745 (ester C=O), 1680 (urethane C=O), 1640 (amide C=O).

3-(4) Synthesis of (2S,3R)-AHMHA-Val-Leu-Asp

Under the same conditions as described in Example 2-(4), 416 mg of Z-(2S,3R)AHMHA-Val-Leu-Asp(OBzl)₂ was hydrogenolysed to give 223 mg of (2S,3R)-AHMHA-Val-Leu-Asp.

Rf: 0.38 (butanol/acetic acid/water=4/1/1, a silica gel as described above).

m.p.: 264°–266° C. [α]$_D^{22}$: −41.7° (c=2.0, CH₃COOH).

Elemental analysis (for C₂₂H₄₀N₄O₈): Found: C, 53.79%; H, 8.63%; N, 11.19%. Calculated: C, 54.08%; H, 8.25%; N, 11.47%.

Example 4

Synthesis of (2S,3R)-AHMHA-Val-Glu-Asp 4-(1) Synthesis of Boc-Glu(OBzl)-Asp(OBzl)₂

Boc-Glu(OBzl) (1.04 g) was subjected to condensation with Asp(OBzl)₂ under the same reaction conditions as presented in Example 1-(1) and then chromatographed on a silica gel column (50 g, same supporting material as described above) using a solvent mixture of benzene and ethyl acetate (mixing ratio 10:1). The recrystallization from a solvent mixture of ether and hexane yielded 1.73 g of crystals of the title compound.

Rf: 0.73 (benzene/ethyl acetate=2/1, a silica gel plate as described above).

m.p.: 69.5°~70.5° C.

[α]$_D^{22}$: −10.7° (c=2.0, CH₃OH).

n.m.r.: δppm (CDCl₃): 1.41 (9H, s, —C(C<u>H</u>₃)₃)

2.0 (2H, m, CH₂—C<u>H</u>₂—CH—$\overset{O}{\underset{\|}{C}}$)

2.4 (2H, m, —$\overset{O}{\underset{\|}{C}}$—C<u>H</u>₂—CH₂—CH—)

2.94 (2H, dd, —$\overset{O}{\underset{\|}{C}}$—CH—C<u>H</u>₂—$\overset{O}{\underset{\|}{C}}$—)

3.9~4.4 (1H, m, —NH—C<u>H</u>—$\overset{O}{\underset{\|}{C}}$—)

4.7~5.1 (1H, m, —NH—C<u>H</u>—$\overset{O}{\underset{\|}{C}}$—)

5.05 (2H, s, —C<u>H</u>₂Ph), 5.10 (4H, s, —CH₂Ph×2), 7.0~7.5 (2H, m, —NH—×2), 7.27, 7.30, 7.33 (15H, each s, —CH₂P<u>h</u>×3).

IR: ν$_{max}^{KBr}$ cm⁻¹:

$$3330(-\underline{NH}-\overset{O}{\underset{\|}{C}}-),$$

1750, 1735 (ester C=O), 1690 (urethane C=O), 1655 (amide C=O).

4-(2) Synthesis of Boc-Val-Glu(OBzl)-Asp(OBzl)₂

As described in Example 1-(2), 1.63 g of Boc-Glu(OBzl)-Asp(OBzl)₂ was treated with trifluoroacetic acid and then condensed with 559 mg of Boc-Val. By silica gel column (20 g, same supporting material as described above) chromatography using a developing solvent system of benzene-ethyl acetate (3/1), 1.38 g of crystals of the title compound was obtained.

Rf: 0.16 (benzene/ethyl acetate=5/1, a silica gel plate as described above).

m.p.: 113°~114° C.

[α]$_D^{22}$: −25.2° (c=2.0, CH₃OH).

n.m.r. δppm (CDCl₂): 0.88, 0.91 (6H, each d, J7 Hz, —CH(C<u>H</u>₃)₂) 1.41 (9H, s, —C(CH₃)₃)

1.8~2.2 (5H, m, >CH—C<u>H</u>₂—C<u>H</u>₂—$\overset{O}{\underset{\|}{C}}$—, —C<u>H</u>(CH₃)₂)

2.94 (2H, dd, >CH—C<u>H</u>₂—$\overset{O}{\underset{\|}{C}}$—)

3.91 (1H, dd, J6Hz, 8Hz—NH—C<u>H</u>—$\overset{O}{\underset{\|}{C}}$—)

4.3~5.0 (2H, m, —NH—C<u>H</u>—$\overset{O}{\underset{\|}{C}}$—)

5.05 (2H, s, C<u>H</u>₂—Ph), 5.10 (4H, s, —C<u>H</u>₂—Ph×2), 5.0~5.3 (1H, m, —NH—), 6.8~7.1 (2H, m, —NH×2), 7.29, 7.3, 7.34 (15H, each s, —CH₂—P<u>h</u>×3).

IR: ν$_{max}^{KBr}$ cm⁻¹:

$$3330(-\underline{NH}-\overset{O}{\underset{\|}{C}}-),$$

1730 (ester C=O), 1685 (urethane C=O), 1650 (amide C=O).

4-(3) Synthesis of Z-(2S,3R)-AHMHA-Val-Glu-(OBzl)-Asp(OBzl)₂

Employing the same procedure as detailed in Example 1-(3), 707 mg of Boc-Val-Glu(OBzl)-Asp(OBzl)₂ was treated with trifluoroacetic acid and then submitted to condensation with 280 mg of Z-(2S,3R)-AHMHA. Crystals of the title compound (343 mg) was recovered by recrystallization from a chloroform-ether mixture.

Rf: 0.53 (benzene/ethyl acetate=1/1, a silica gel plate as described above).

m.p.: 157°~159° C.

[α]$_D^{22}$: −22.1° (c=2.0, CH₃OH).

n.m.r. δppm (CDCl₃): 0.75~0.95 (12H, m, —CH(CH₃)₂×2), 1.2~1.7 (2H, m, —CH(CH₃)₂×2), 1.7~2.2 (4H, m, —NH—C<u>H</u>—CH₂—CH(CH₃)₂, —C<u>H</u>₂—CH₂CO—)

2.2~2.5 (2H, m, —CH₂—C<u>H</u>₂—$\overset{O}{\underset{\|}{C}}$—)

2.7~3.0 (2H, m, >CH—C<u>H</u>₂—$\overset{O}{\underset{\|}{C}}$—)

3.8~5.0 (4H, m, —NH—C<u>H</u>—$\overset{O}{\underset{\|}{C}}$ × 4)

5.0, 5.05 (8H, s, —CH₂Ph×4), 5.4~5.8 (1H, m, —NH), 7.1~7.8 (3H, m, —NH×3), 7.25, 7.28 (20H, —CH₂Ph×4).

IR: $\nu_{max}^{KBr}$ cm⁻¹:

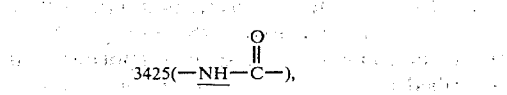

1735 (ester C=O), 1680 (urethane C=O), 1640 (amide C=O).

4-(4) Synthesis of (2S,3R)-AHMHA-Val-Glu-Asp

Under the same reaction conditions as detailed in Example 1-(4), 341 mg of Z-(2S,3R)-AHMHA-Val-Glu(OBzl)-Asp(OBzl)₂ was hydrogenolysed to provide 247 mg of crystals of the title compound.

Rf: 0.39 (butanol/acetic acid/water=4/1/1, a silica gel plate as described above).

m.p.: 159°-161° C.

$[\alpha]_D^{22}$: −29.4° (c=1.0, 80% CH₃COOH in water).

Elemental analysis (for C₂₂H₄₀N₄O₈): Found: C, 54.35%; H, 8.21%; N, 11.24%. Calculated: C, 54.08%; H, 8.25%; N, 11.47%.

Example 5

Synthesis of (2S,3R)-AHMHA-Thr-Val-Asp 5-(1) Synthesis of Boc-Val-Asp(OBzl)₂

Under the same reaction conditions as specified in Example 1-(1), the condensation product of 4.0 g of Boc-Val with 8.94 g of Asp(OBzl)₂ was chromatographed on a silica gel column (100 g, same supporting material as described above) using a developing solvent system of benzene and ethyl acetate (5/1) and then recrystallized from a solvent mixture of chloroform and hexane to give 8.77 g of crystals of the title compound.

Rf: 0.39 (benzene/ethyl acetate=5/1, a silica gel plate as described above).

m.p.: 80°~81° C.

$[\alpha]_D^{22}$: −24.6° (c=2.0, CH₃OH).

n.m.r. δppm (CDCl₃): 0.8, 0.92 (6H, each d, J5 Hz, —CH(CH₃)₂), 1.42 (9H, s, —C(CH₃)₃), 1.9~2.3 (1H, m, —CH(CH₃)₂),

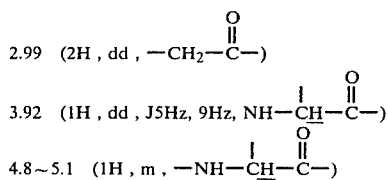

5.05, 5.12 (4H, each s, —CH₂—Ph×2), 6.7~7.0 (1H, m, —NH), 7.2~7.4 (1H, m, —NH), 7.30 (10H, s, —CH₂—Ph×2).

IR: $\nu_{max}^{KBr}$ cm⁻¹:

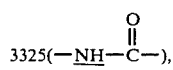

1730 (ester C=O), 1690 (urethane C=O), 1650 (amide C=O).

5-(2) Synthesis of Boc-Thr(Bzl)-Val-Asp(OBzl)₂

By the same procedure as detailed in Example 1-(2), 1.0 g of Boc-Val-Asp(OBzl)₂ was treated with trifluoroacetic acid and then subjected to condensation with 535 mg of Boc-Thr(Bzl). Silica gel column (25 g, same supporting material as described above) chromatography with a developing solvent mixture of benzene and ethyl acetate (10/1) followed by recrystallization in an ether-hexane mixture yielded 611 mg of the title compound.

Rf: 0.86 (benzene/ethyl acetate=2/1, a silica gel plate as described above).

m.p.: 136°-137° C.

$[\alpha]_D^{22}$: −17.5° (c=2.0, CH₃OH).

IR: $\nu_{max}^{KBr}$ cm⁻¹:

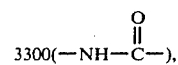

1730 (ester C=O), 1685 (urethane C=O), 1640 (amide C=O)

n.m.r. δppm (CDCl₃): 0.75 and 0.87 (6H, each d, J5.5 Hz, —CH(CH₃)₂), 1.1~1.2

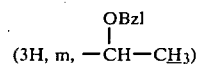

1.43 (9H, s, —O—C(CH₃)₃),

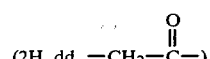

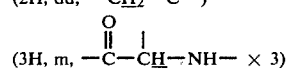

5.05 (2H, ABq, —CH₂Ph), 5.47, 6.03, 6.95 (3H, m, —NH—×3), 7.29 (5H, s, —CH₂Ph).

5-(3) Synthesis of (2S,3R)-AHMHA-Thr-Bzl)-Val-Asp(OBzl)₂

By the same procedure as described in Example 1-(2), 520 mg of Boc-Thr(Bzl)-Val-Asp(OBzl)₂ was treated with trifluoroacetic acid and then subjected to condensation with 187 mg of Z-(2S,3R)-AHMHA. The condensation product was charged on a silica gel column (30 g, same supporting material as described above) and eluted with a developing solvent mixture of benzene and ethyl acetate (3/1). By recrystallization from an ether-hexane mixture, 386 mg of the title compound in the crystalline form was obtained.

Rf: 0.37 (benzene/ethyl acetate=1/1, a silica gel plate as described above).

m.p.: 93.0°-96.0° C.

$[\alpha]_D^{22}$: −18.5° (c=1.0, CH₃OH).

IR: $\nu_{max}^{KBr}$ cm⁻¹:

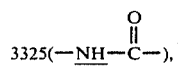

1730 (ester C=O), 1630 (amide C=O)

n.m.r δppm (CDCl₃):

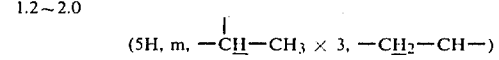

-continued 2.89 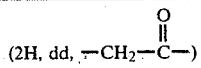
(2H, dd, —CH$_2$—C—)

3.9~4.5 (3H, m, —NH—CH—×3), 4.5~4.9 (2H, m, —NH—CH—×2), 4.55 (2H, ABq, —CH$_2$Ph), 5.02 (4H, s, —CH$_2$Ph×2), 5.09 (2H, s, —CH$_2$Ph), 5.3~5.7 (2H, m, —NH), 6.8~7.7 (3H, m, —NH×3), 7.29 (20H, s, —CH$_2$Ph×4).

5-(4) Synthesis of (2S,3R)-AHMHA-Thr-Val-Asp

Under the same conditions of hydrogenolysis as detailed in Example 1-(4), 200 mg of the title compound was recovered from 386 mg of Z-(2S,3R)-AHMHA-Thr(Bzl)-Val-Asp(OBzl)$_2$ by using 10% palladium-carbon.

Rf: 0.41(butanol/acetic acid/water=4/1/1, a silica gel plate as described above).

m.p.: over 180° C. under decomposition.

$[\alpha D]_D^{22}$: −39.1° (C=0.6, CH$_3$COOH).

Elemental analysis (for C$_{20}$H$_{36}$N$_4$O$_9$): Found: C, 50.27%; H, 7.95%; N, 11.49%. Calculated: C, 50.41%; H, 7.62%; N, 11.76%.

Example 6

Synthesis of (2S,3R)-AHMHA-Leu-Val-Asp 6-(1) Synthesis of Boc-Leu-Val-Asp(OBzl)$_2$ Boc-Val-Asp(OBzl)(708 mg) prepared by the same method as presented in Example 5-(1) was treated with trifluoroacetic acid under the conditions specified in Example 1-(2) and then subjected to condensation with 397 mg of Boc-Leu. Silica gel column (30 g, same supporting material as described above) chromatography with a developing solvent mixture of benzene and ethyl acetate (3/2) gave 673 mg of crystals of the title compound.

Rf: 0.56 (benzene/ethyl acetate=3/2, a silica gel plate as described above).

m.p.: 135°–136° C.

$[\alpha]_D^{22}$: −36.7° (c=2.0, CH$_3$OH).

IR: $\nu_{max}^{KBr}$ cm$^{-1}$:

O
‖
3310(—NH—C—), 1730 (ester C=O), 1690 (urethane C=O), 1640 (amide C=O).

n.m.r. δppm (CDCl$_3$): 0.8~1.1 (12H, m, —CH(CH$_3$)$_2$×2), 1.42 (9H, s, —C—(CH$_3$)$_3$), 1.5~2.3
(4H, m, —CH$_2$—CH<, —CH(CH$_3$)$_2$ × 2)

2.95 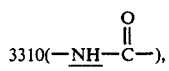
(2H, dd, —CH$_2$—C—)

4.0~4.6
(2H, m, —NH—CH—C— × 2)

4.65~5.4
(2H, m, —NH—CH—C—)

5.06, 5.11 (4H, each s, —CH$_2$Ph×2), 6.7~7.2 (2H, m, —NH—×2), 7.32 (10H, s, —CH$_2$Ph×2).

6-(2) Synthesis of Z-(2S,3R)-AHMHA(Z)-Leu-Val-Asp(OBzl)$_2$

By the same method as detailed in Example 1-(2), 509 mg of Boc-Leu-Val-Asp(OBzl)$_2$ was treated with trifluoroacetic acid and then condensed with Z-(2S,3R)-AHMHA(Z) (285 mg). After column chromatography on silica gel (30 g, same supporting material as described above) with a developing solvent system of benzene and ethyl acetate (3/1) 490 mg of the title compound was obtained.

Rf: 0.45(benzene/ethyl acetate=2/1, a silica gel plate as described above).

m.p.: 140°–143° C.

$[\alpha]_D^{22}$: −17.6° (c=1.0, CH$_3$OH/CHCl$_3$=5/1).

IR: $\nu_{max}^{KBr}$ cm$^{-1}$:

O
‖
3320(—NH—C—), 1750 (ester C=O), 1695 (urethane C=O), 1645 (amide C=O).

n.m.r. δppm (CDCl$_3$): 0.7~0.95 (18H, —CH(CH$_3$)$_2$×3), 1.1~2.3
(7H, m, —CH$_2$—CH< × 2, —CH(CH$_3$)$_2$ × 3)

2.92 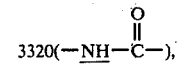
(2H, dd, CH$_2$—C—O—)

4.1~4.6
(4H, m, NH—CH—C— × 4)

4.8~5.0
(1H, m, NH—CH—C—)

5.0~5.2
(9H, —CH$_2$—Ph × 4, —CH—O—C)

5.2~5.6 (1H, —NH—), 6.5~7.0 (3H, —NH—×3), 7.3~7.4 (20H, CH$_2$—Ph×4).

6-(3) Synthesis of (2S,3R)-AHMHA-Leu-Val-Asp

Under the same operational conditions as presented in Example 1-(4), 200 mg of Z-(2S,3R)-AHMHA(Z)-Leu-Val-Asp(OBzl)$_2$ was hydrogenolysed to give 72 mg of the title compound.

Rf: 0.42 (butanol/acetic acid/water=4/1/1, a silica gel plate as described above).

m.p.: over 249° C. under decomposition.

$[\alpha]_D^{22}$: −30.2° (c=1.0, CH$_3$COOH).

Elemental analysis (for C$_{22}$H$_{40}$N$_4$O$_8$): Found: C, 53.75%; H, 8.18%; N, 11.28%. Calculated: C, 54.08%; H, 8.25%; N, 11.47%.

Example 7

Synthesis of (2S,3R)-AMHMA-Lys-Val-Asp 7-(1) Synthesis of Boc-Lys(Z)-Val-Asp(OBzl)$_2$ Under the same reaction conditions as specified in Example 1-(2), 1.0 g of Boc-Val-Asp(OBzl)$_2$ prepared by the method detailed in Example 5-(1) was treated with trifluoroacetic acid and then subjected to condensation with Boc-Lys(Z). Silica gel column (30 g, same supporting material as described above) chromatography with a developing solvent mixture of benzene and ethyl acetate (3/2) yielded 866 mg of crystals of the title compound.

Rf: 0.26 (benzene/ethyl acetate=2/1, a silica gel plate as described above).
m.p.: 122°–124° C.
$[\alpha]_D^{22}$: −21.2° (c=3.0, CH$_3$OH).
IR: $\nu_{max}^{KBr}$ cm$^{-1}$:

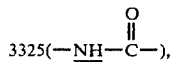

1740 (ester C=O), 1685 (urethane C=O), 1640 (amide C=O).
n.m.r. δppm (CDCl$_3$): 0.86 and 0.90 (6H, each d, J7 Hz, —CH(C$\underline{H}_3$)$_2$), 1.41 (9H, s, —C(CH$_3$)$_3$), 1.2~2.1 (7H, m, —(CH$_2$)$_3$—, —C$\underline{H}$(CH$_3$)$_2$), 2.8~3.3 (4H, m, —C$\underline{H}_2$—NH—, —C$\underline{H}_2$—CO—),

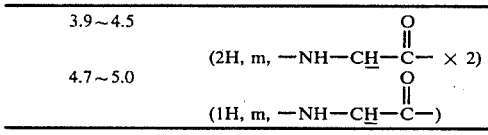

5.05~5.1 (6H, —C$\underline{H}_2$—Ph×3), 5.3~5.45 (1H, m, —N$\underline{H}$—), 6.7~7.2 (2H, m, —NH—×2), 7.33 (15H, —CH$_2$P$\underline{h}$×3).

7-(2) Synthesis of Z-(2S,3R)-AHMHA(Z)-Lys(Z)-Val-Asp(OBzl)$_2$

Boc-Lys(Z)-Val-Asp(OBzl)$_2$ (534.4 mg) was treated with trifluoroacetic acid and then subjected to condensation with 258 mg of Z-(2S,3R)-AHMHA(Z) by the same procedure as specified in Example 1-(3). The condensation product was purified by silica gel column (30 g, same supporting material as described above) chromatography with a developing solvent system of benzene and ethyl acetate (2/1) to yield 510 mg of the title compound.
Rf: 0.53 (benzene/ethyl acetate=1/1, a silica gel plate as described above).
$[\alpha]_D^{22}$: −9.6° (c=0.85, CHCl$_3$/CH$_3$OH=1/6).
IR: $\nu_{max}^{KBr}$ cm$^{-1}$:

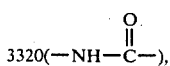

1730 (ester C=O), 1690 (urethane C=O), 1640 (amide C=O)
n.m.r. δppm (CDCl$_3$): 0.75~0.95 (12H, —CH(CH$_3$)$_2$×2), 1.1~2.2 (10H, —(CH$_2$)$_3$—, —C$\underline{H}$(CH$_3$)$_2$×2, —C$\underline{H}_2$—CH(CH$_3$)$_2$).

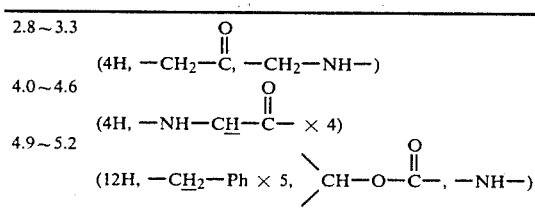

6.5~7.0 (4H, —NH—×4), 7.2~7.4 (25H, CH$_2$—P$\underline{h}$×5).

7-(3) Synthesis of (2S,3R)-AHMHA-Lys-Val-Asp
Hydrogenolysis of 230 mg of Z-(2S,3R)-AHMHA(Z)-Lys(Z)-Val-Asp(OBzl)$_2$ under the operational conditions specified in Example 1-(4) gave 84 mg of the above-listed compound. Rf: 0.1 (butanol/acetic acid/water=4/1/1, a silica gel plate as described above).
m.p.: over 170° C. under decomposition.
$[\alpha]_D^{22}$: −28.6° (c=1.0, CH$_3$COOH).
Elemental analysis (for C$_{22}$H$_{40}$N$_5$O$_8$): Found: C, 52.72%; H, 8.54%, N, 13.57%. Calculated: C, 52.47%; H, 8.21%; N, 13.91%.

Example 8

Synthesis of (2S,3R)-AHMHA-Glu-Val-Asp 8-(1) Synthesis of Boc-Glu(OBzl)-Val-Asp(OBzl)$_2$
By the same procedure as presented in Example 1-(2), 1.0 g of Boc-Val-Asp(OBzl)$_2$ was treated with trifluoroacetic acid and then submitted to condensation with Boc-Glu(OBzl). After column chromatography on silica gel (30 g, same supporting material as described above) with a developing solvent system of benzene and ethyl acetate (3/1), 780 mg of the title compound was obtained.
Rf: 0.51 (benzene; ethyl acetate=2/1, a silica gel plate as described above).
m.p.: 124°–126° C.
$[\alpha]_D^{22}$: −27.7° (c=1.5, CH$_3$OH).
IR: $\nu_{max}^{KBr}$ cm$^{-1}$:

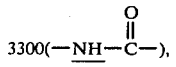

1730 (ester C=O), 1690 (urethane C=O), 1640 (amide C=O).
n.m.r. δppm (CDCl$_3$): 0.85 and 0.88 (6H, each d, J6.5 Hz, CH(C$\underline{H}_3$)$_2$), 1.4 (9H, s, —CH(C$\underline{H}_3$)$_3$), 1.8~2.3

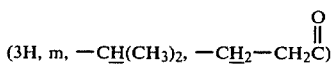

2.3~2.7 (2H, m, —CH$_2$—C$\underline{H}_2$—CO—), 2.95

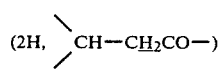

4.0~5.0 (3H, —NH—C$\underline{H}$—CO—×3), 5.05~5.1 (6H, —C$\underline{H}_2$Ph×3), 5.2~5.5 (1H, —NH—), 6.8~7.1 (2H, —NH—×2), 7.3 (15H, —CH$_2$P$\underline{h}$×3).

8-(2) Synthesis of Z-(2S,3R)-AHMHA(Z)-Glu(OBzl)-Val-Asp(OBzl)$_2$

Under the same operational conditions as detailed in Example 1-(2), 510 mg of Boc-Glu(OBzl)-Val-Asp(OBzl)$_2$ was treated with trifluoroacetic acid and then condensed with 270 mg of Z-(2S,3R)-AHMHA(Z). The condensation product was purified by column chromatography on silica gel (30 g, same supporting material as described above) using an elution solvent system of benzene and ethyl acetate (2/1) to provide 500 mg of the title compound.
Rf: 0.75 (benzene/ethyl acetate=1/1, a silica gel plate as described above).
$[\alpha]_D^{22}$: −10.8° (c=1.0, CH$_3$OH).
IR: $\nu_{max}^{KBr}$ cm$^{-1}$:

3300(—N<u>H</u>—C(=O)—), 1740 (ester C=O), 1690 (urethane C=O), 1630 (amide C=O).

n.m.r. δppm (CDCl₃): 0.8~0.9 (12H, —CH(C<u>H</u>₃)₂×2), 1.0~1.8 (3H, —C<u>H</u>(CH₃)₂×2, —C<u>H</u>₂—CH(CH₃)₂),

| | |
|---|---|
| 1.8~2.2 | (2H, —CH₂—C<u>H</u>₂—C(=O)—) |
| 2.2~2.6 | (2H, —CH₂—C<u>H</u>₂—C(=O)—) |
| 2.8~3.1 | (2H, \CH—C<u>H</u>₂—C(=O)) |
| 3.9~4.6 | (3H, —NH—C<u>H</u>—C(=O) × 3) |
| 4.7~5.1 | (2H, —NH—C<u>H</u>—C(=O), \CH—O—C(=O)—) |

5.0~5.2 (10H, —C<u>H</u>₂—Ph×5), 5.1~5.4 (1H, —NH—), 6.8~7.1 (3H, —NH—×3), 7.2~7.4 (25H, —CH₂P<u>h</u>×5).

8-(3) Synthesis of (2S,3R)-AHMHA-Glu-Val-Asp

The same conditions of hydrogenolysis as detailed in Example 1-(4) yielded 65 mg of the title compound from 190 mg of Z-(2S,3R)-AHMHA(Z)-Glu(OBzl)-Val-Asp(OBzl)₂. Rf: 0.22 (butanol/acetic acid/water=4/1/1, a silica gel plate as described above).

m.p.: over 165° C. under decomposition.

[α]$_D^{22}$: −27.2° (c=0.5, CH₃COOH).

Elemental analysis (for C₂₈H₄₂N₄O₁₀): Found: C, 50.36%; H, 7.12%; N, 10.86%. Calculated: C, 49.99%; H, 7.19%; N, 11.11%.

Example 9

Synthesis of (2S,3R)-AHMHA-Val-Thr-Phe 9-(1) Synthesis of Boc-Thr(Bzl)-Phe(OBzl)

By the same method as detailed in Example 1-(1), 2.9 g of Boc-Thr(OBzl) and 4.0 g of Phe(OBzl).TosOH were subjected to condensation and then purified by column chromatography on silica gel (50 g, Kiesel gel 60, E. Merck) using a developing solvent mixture of benzene and ethyl acetate (10/1) to provide 4.8 g of the title compound.

m.p.: 138°–139° C.

[α]$_D^{21}$: −4.0° (c=1.0, CH₃OH).

IR: $\nu_{max}^{KBr}$ cm⁻¹: 3320 (—N<u>H</u>—CO—), 1730 (ester C=O), 1680 (urethane C=O), 1660 (amide C=O).

n.m.r. δppm (CDCl₃): 1.14

(3H, d, J6H, \CH—C<u>H</u>₃)

1.4 (9H, s, —C(CH₃)₃), 3.02 (2H, d, J6 Hz, —C<u>H</u>₂Ph), 3.9~5.0

(3H, —NH—C<u>H</u>—C(=O)— × 2, \C<u>H</u>—OCH₂Ph)

4.53 (2H, —OC<u>H</u>₂Ph), 5.09 (2H, —OC<u>H</u>₂Ph), 5.3~5.5 (1H, —NH—), 6.8~7.3 (16H, —NH—, —CH₂P<u>h</u>×3).

9-(2) Synthesis of Boc-Val-Thr(OBzl)-Phe(OBzl)

Under the same reaction conditions as specified in Example 1-(2), 4.8 g of Boc-Thr(OBzl)-Phe(OBzl) was treated with trifluoroacetic acid and then subjected to condensation with 1.9 g of Boc-Val. By column chromatography on silica gel (Kieselgel 60, 60 g) with an eluant of benzene and ethyl acetate (5/1), 4.8 g of the title compound was obtained.

Rf: 0.28 (benzene/ethyl acetate=5/1, a silica gel plate as described above).

[α]$_D^{22}$: −13.7° (c=1.0, CH₃OH).

m.p.: 137°–138° C.

IR: $\nu_{max}^{KBr}$ cm⁻¹: 3280 (—N<u>H</u>—CO—), 3740 (ester C=O), 1690 (urethane C=O), 1640 (amide C=O).

n.m.r. δppm (CDCl₃): 0.8~1.0

(9H, —CH(C<u>H</u>₃)₂, \CH—C<u>H</u>₃)

1.4 (9H, —C(C<u>H</u>₃)₃), 1.5~2.2 (1H, —C<u>H</u>(CH₃)₂), 3.0 (2H, —C<u>H</u>₂Ph), 3.8~4.9

(4H, —NH—C<u>H</u>—CO— × 3, \C<u>H</u>—O—CH₂Ph)

4.52 (2H, —O—C<u>H</u>₂Ph), 5.08 (2H, —O—CH₂Ph), 4.9~5.2 (1H, —NH—), 6.8~7.3 (17H, —CH₂P<u>h</u>×3, —NH—×2).

9-(3) Synthesis of Z-(2S,3R)-AHMHA-Val-Thr(OBzl)-Phe(OBzl)

By the same procedure as presented in Example 1-(3), 600 mg of Boc-Val-Thr(OBzl)-Phe(OBzl) was treated with trifluoroacetic acid and then condensed with 259 mg of Z-(2S,3R)-AHMHA. Recrystallization of the condensation product from a solvent mixture of chloroform and hexane provided 650 mg of the title compound.

Rf: 0.37 (benzene/ethyl acetate=1/1, a silica gel plate as described above).

m.p.: 168°–169° C.

[α]$_D^{21}$: −11.9° (c=0.6, CHCl₃/CH₃OH=3/1).

IR: $\nu_{max}^{KBr}$ cm⁻¹: 3290 (—N<u>H</u>—CO—), 1730 (ester C=O), 1680 (urethane C=O), 1630 (amide C=O).

n.m.r. δppm (CDCl₃): 0.8~1.0

(15H, —CH(C<u>H</u>₃)₂ × 2, \CH—C<u>H</u>₃)

1.1~1.7 (4H, —C<u>H</u>(CH₃)₂×2, —C<u>H</u>₂—CH(CH₃)₂), 3.0 (2H, —C<u>H</u>₂Ph), 3.8~4.9

(6H, —NH—C<u>H</u>—CO— × 3, —NH—C<u>H</u>—C<u>H</u>—OH)

4.5 (2H, —O—C<u>H</u>₂Ph), 5.0 and 5.05 (4H, —O—C<u>H</u>₂Ph), 5.2~5.7 (2H, —NH—×2), 6.8~7.3 (22H, —N<u>H</u>—×2, CH₂P<u>h</u>×4)

9-(4) Synthesis of (2S,3R)-AHMHA-Val-Thr-Phe

The same hydrogenolysis conditions as described in Example 2-(4) produced 100 mg of (2S,3R)-AHMHA-Val-Thr-Phe from 300 mg of Z-(2S,3R)-AHMHA-Val-Thr(OBzl)-Phe(OBzl).

Rf: 0.55 (butanol/acetic acid/water=4/1/1, a silica gel plate as described above).

m.p.: 159°–161° C.

$[\alpha]_D^{21}$: −14.2° (c=0.5, CH$_3$COOH).

Elemental analysis (for C$_{25}$H$_{40}$N$_4$O$_7$): Found: C, 58.76%; H, 8.06%; N, 10.95%. Calculated C, 59.04%; H, 7.93%; N, 11.02%.

Example 10

Synthesis of (2S,3R)-AHMHA-Lys-Val-Val 10-(1) Preparation of Boc-Val-Val(OBzl)

Using 1.1 g of Boc-Val and 2.0 g of Val-OBzl.TosOH, the condensation reaction as specified in Example 1-(1) was repeated. Column chromatography on silica gel (Kieselgel 60, 50 g) with a developing solvent of benzene and ethyl acetate (mixing ratio 10:1) provided 2.0 g of the title compound.

Rf: 0.41 (benzene/ethyl acetate=5/1, a silica gel plate as described above).

$[\alpha]_D^{21}$: −49.0° (c=2.0, CH$_3$OH).

IR: $\nu_{max}^{KBr}$ cm$^{-1}$: 3310 (—NH—CO—), 1740 (ester C=O), 1685 (urethane C=O), 1655 (amide C=O).

n.m.r. δppm (CDCl$_3$): 0.8~1.0 (12H, —CH(CH$_3$)$_2$×2), 1.42 (9H, s, —C(CH$_3$)$_3$), 1.7~2.5 (2H, m, —CH(CH$_3$)$_2$×2), 3.93 (1H, dd, J9 Hz, 7 Hz, —NH—CH—CO—), 4.57 (1H, dd, J9 Hz, 5 Hz, —NH—CH—CO—), 5.0~5.3 (1H, —NH—), 5.15 (2H, s, —O—CH$_2$Ph), 6.4~6.6 (1H, —NH—), 7.33 (5H, s, —OCH$_2$Ph).

10-(2) Preparation of Boc-Lys(Z)-Val-Val(OBzl)

Using the same method as detailed in Example 1-(2), 1.4 g of Boc-Val-Val(OBzl) was treated with trifluoroacetic acid and then submitted to condensation with Boc-Lys(Z)(1.3 g). After silica gel column (60 g, Kieselgel 60) chromatography with a developing solvent system of benzene and ethyl acetate (mixing ratio 4:1), 2.0 g of the title compound was obtained.

Rf: 0.48 (benzene/ethyl acetate=1/1, a silica gel plate as described above).

m.p.: 145°–146° C.

$[\alpha]_D^{21}$: −47.5° (c=1.0, CH$_3$OH).

IR: $\nu_{max}^{KBr}$ cm$^{-1}$: 3320 (—NH—CO—), 1730 (ester C=O), 1685 (urethane C=O), 1640 (amide C=O).

n.m.r. δppm (CDCl$_3$): 0.75~1.0 (12H, —CH(CH$_3$)$_2$×2), 1.4 (9H, —C(CH$_3$)$_3$), 1.3~2.3 (8H, —(CH$_2$)$_3$—, —CH(CH$_3$)$_2$×2), 3.0~3.3 (2H, —CH$_2$NH—), 3.9~4.8 (3H, —NH—CH—CO—×3), 5.05~5.15 (4H, CH$_2$Ph×2), 5.0~5.6 (2H, —NH—×2), 6.8~7.1 (2H, —NH—×2), 7.3 (10H, —CH$_2$Ph×2).

10-(3) Preparation of Z-(2S,3R)-AHMHA-Lys(Z)-Val-Val(OBzl)

By the same procedure as specified in Example 1-(3) 600 mg of Boc-Lys(Z)-Val-Val(OBzl) was treated with trifluoroacetic acid and then submitted to condensation with 222 mg of Z-(2S,3R)-AHMHA. The above-listed compound (500 mg) was produced by recrystallization in a solvent mixture of chloroform and hexane.

Rf: 0.15 (benzene/ethyl acetate=1/1, a silica gel plate as described above).

m.p: 176°–178° C.

$[\alpha]_D^{21}$: −35.1° (c=1.0, CH$_3$OH).

IR: $\nu_{max}^{KBr}$ cm$^{-1}$: 3290(—NH—CO—), 1730(ester C=O), 1685(urethane C=O), 1635(amide C=O).

n.m.r. δppm (CDCl$_3$): 0.7~1.0 (18H, —CH(CH$_3$)$_2$×3), 1.1~2.3 (11H, —CH(CH$_3$)$_2$×3, —CH$_2$CH(CH$_3$)$_2$, —(CH$_2$)$_3$—), 2.8~3.2 (2H, —CH$_2$NH—), $$4.0\sim4.9 (6H, -NH-\underset{|}{C}H-CO-\times 3, -NH-\underset{|}{C}H-\underset{|}{C}H-OH)$$

5.0~5.2 (6H, —CH$_2$Ph×3), 5.2~5.8 (4H, —NH—×4), 7.2~7.4 (16H, —NH—, —CH$_2$Ph×3).

10-(4) Preparation of (2S,3R)-AHMHA-Lys-Val-Val

Three hundred milligrams of Z-(2S,3R)-AHMHA-Lys(Z)-Val-Val(OBzl) was hydrogenolysed under the same operational conditions as detailed in Example 1-(4) to yield 109 mg of (2S,3R)-AHMHA-Lys-Val-Val.

Rf: 0.25 (butanol/acetic acid/water=4/1/1, a silica gel plate as described above).

m.p.: over 170° C. under decomposition.

$[\alpha]_D^{21}$: −39.6° (c=0.7, CH$_3$COOH).

Elemental analysis (for C$_{23}$H$_{45}$N$_5$O$_6$): Found: C, 56.51%; H, 9.17%; N, 13.98%. Calculated: C, 56.65%; H, 9.30%; N, 14.36%.

Example 11

Synthesis of (2S,3R)-AHMHA-Val-Val-Thr 11-(1) Synthesis of Boc-Val-Thr(Bzl)OBzl

Thr(Bzl)OBzl.½oxalate (406.4 mg) was dissolved in 50 ml of ethyl acetate and washed three times with 20 ml each of 4% sodium bicarbonate and twice with 20 ml each of saturated solution of sodium chloride. After the organic solution was dehydrated over anhydrous sodium sulfate, the solvent was removed by evaporation under reduced pressure to give Thr(Bzl)OBzl. The total amount of Thr(Bzl)OBzl thus prepared, 217.3 mg of Boc-Val and 148.6 mg of HOBt were dissolved in 10 ml of THF and cooled with ice. After 227 mg of DCCD was added, the reaction mixture was allowed to react for 2 hours under cooling with ice and for one hour at room temperature. The precipitates of DCU were filtered off and the solvent was removed by evaporation in vacuo. The evaporation residue was dissolved in 50 ml of ethyl acetate and extracted three times with 20 ml each of 10% citric acid, three times with 20 ml each of 4% sodium bicarbonate and twice with 20 ml each of saturated solution of sodium chloride. The organic solution was dehydrated over a suitable amount of anhydrous sodium sulfate and the ethyl acetate was evaporated off under reduced pressure. The evaporation residue was subjected to silica gel column (10 g, Kiesel gel 60, 70–230 mesh, E. Merck) chromatography using a developing solvent system of chloroform and methanol (40/1) to give 305 mg of the title compound.

n.m.r. δppm (CDCl$_3$): 0.91 and 0.95 (6H, each d, J=7 Hz, —CH(CH$_3$)$_2$), 1.18

$$(3H, d, -O-\underset{|}{C}H-CH_3)$$

1.40 (9H, s, —C(CH$_3$)$_3$), 1.9~2.3 (1H, m, —CH(CH$_3$)$_2$), 3.8~4.3 (2H, m, —CH(CH$_3$)—OBzl, —NH—CH—CO—), 4.1~4.6 (2H, ABq., J=jem12 Hz, —OCH$_2$Ph), 4.70 (1H, dd, J=5 Hz, 9 Hz, —NHCHCO—), 5.06 (2H, s, —COOCH$_2$Ph), 5.1~5.3 (1H, —NH—), 6.45~6.7 (1H, —NH—), 7.22 (10H, s, —CH$_2$Ph×2).

11-(2) Synthesis of Boc-Val-Val-Thr(Bzl)OBzl

By treatment with trifluoroacetic acid under the same reaction conditions as described in Example 1-(2), 305 mg of Boc-Val-Thr(Bzl)OBzl was converted to its free amine. This amine was condensed with 168 mg of Boc-Val to yield 438 mg of crystals of the title compound.

Rf: 0.94 (benzene/acetone=4/1, a silica gel plate as described above).

n.m.r. δppm (CDCl$_3$): 0.8~1.05 (12H, m, —CH(CH$_3$)$_2$×2), 1.18

(3H, d, J6Hz, >CH—CH$_3$)

1.42 (9H, s, —C(CH$_3$)$_3$), 1.8~2.3 (2H, m, —CH(CH$_3$)$_2$×2), 3.7~4.5 (3H, m, —CH(CH$_3$)—OBzl, —NH—CH—CO—×2), 4.36 (2H, ABq, —O—CH$_2$Ph), 4.6~4.8 (1H, m, —NH—CH—CO—), 5.06 (2H, s, —CO$_2$—CH$_2$Ph), 5.1~5.25 (1H, —NH—), 6.5~6.9 (2H, —NH—×2), 7.25 (10H, s, —CH$_2$Ph×2).

11-(3) Synthesis of Z-(2S,3R)-AHMHA-Val-Val-Thr(Bzl)OBzl

Boc-Val-Val-Thr(Bzl)OBzl(418 mg) was treated with trifluoroacetic acid under the same reaction conditions as specified in Example 1-(3) to provide its free amine, from which 246.1 mg of the title compound was produced by condensation with 161.8 mg of Z-(2S,3R)-AHMHA.

n.m.r. δppm (CD$_3$COCD$_3$): 0.75~1.0 (18H, m, —CH(CH$_3$)$_2$×3), 1.20

(3H, d, J6.0Hz, >CH—CH$_3$)

1.3~1.7 (5H, m, —CH(CH$_3$)$_2$×3, —CH$_2$—CH(CH$_3$)$_2$), 4.0~4.8

(7H, m, —NH—CH— ×4, —NH—CH—CH$_2$—,
  |
  OH
  —CH(CH$_3$)—OBzl)

5.0 and 5.12 (4H, each s, —CH$_2$Ph×2), 5.2~5.4 (1H, m, NH—), 7.22 (5H, s, —CH$_2$Ph), 7.29 (10H, s, —CH$_2$Ph×2), 7.3~7.6 (3H, m, —NH—×3).

11-(4) Synthesis of (2S,3R)-AHMHA-Val-Val-Thr

Z-(2S,3R)-AHMHA-Val-Val-Thr(Bzl)OBzl(246.1 mg) and 50 mg of 5% palladium-charcoal catalyst was suspended in a solvent mixture of methanol, acetic acid and water (4/2/1) and shaken for catalytic reduction at room temperature in a hydrogen atmosphere. After the catalyst was separated by filtration, the filtrate was diluted with water and evaporated to dryness under reduced pressure to yield 137.4 mg of the title compound.

Rf: 0.62 (butanol/acetic acid/water=4/1/2, a silica gel plate as described above).

m.p.: 229.0° C.

[α]$_D^{21}$: −53.2° (c=0.5, CH$_3$COOH).

Elemental analysis (for C$_{21}$H$_{40}$N$_4$O$_7$): Found: C, 54.62%; H, 8.83%; N, 12.05%. Calculated: C, 54.76%; H, 8.75%; N, 12.17%.

Example 12

Synthesis of (2S,3R)-AHMHA-Val-Val-Pro 12-(1) Preparation of Boc-Val-Val

Two grams of Boc-Val-Val(OBzl) which was synthesized by the same method as described in Example 10-(1) was dissolved in 50 ml of methanol and then subjected to catalytic reduction overnight in the presence of 300 mg of 10% palladium-charcoal catalyst. After the catalyst was removed by filtration, the total volume of the filtrate was evaporated to dryness under reduced pressure to provide 1.53 g of the aimed product.

n.m.r. δppm (CDCl$_3$): 0.95 (12H, d, J7 Hz, —CH(CH$_3$)$_2$×2), 1.42 (9H, s, —C(CH$_3$)$_3$), 1.8~2.4 (2H, m, —CH(CH$_3$)$_2$×2), 3.8 ~ 4.1 (1H, m, —NH—CH—CO—)
                        |

4.4 ~ 4.7 (1H, m, —NH—CH—CO—)
                        |

6.4~7.2 (2H, m, —NH×2).

12-(2) Preparation of Boc-Val-Val-Pro(OBzl)

To a mixture of 1.17 g of Pro(OBzl).HCl and 540 μl of NMM in 40 ml of dimethylformamide (abbreviated DMF hereafter) and 20 ml of THF, 1.53 g of Boc-Val-Val and then 0.72 g of HOBt were added under cooling with ice. DCCD(1.10 g) was further added to the solution under cooling with ice and then reacted for 2 hours at 0° C. and for one hour at room temperature. After precipitates of DCU thus formed were filtered off, the filtrate was evaporated to dryness under reduced pressure. The evaporation residue was dissolved in 370 ml of ethyl acetate and was washed three times with 100 ml each of 10% citric acid, three times with 100 ml each of 4% sodium bicarbonate and twice with 80 ml each of saturated solution of sodium chloride. The organic solution was dehydrated over anhydrous sodium sulfate. After the sodium sulfate was removed by filtration, the filtrate was evaporated to dryness to provide 1.16 g of the aimed compound.

n.m.r. δppm (CDCl$_3$): 0.85~1.05 (12H, m, —CH(CH$_3$)$_2$×2), 1.42 (9H, s, —C(CH$_3$)$_3$), 1.7 ~ 2.3 (6H, m, —CH(CH$_3$)$_2$ × 2, —(CH$_2$)$_2$—CH—CO—)
3.4 ~ 4.1 (2H, m, —N—CH$_2$—)
                   |

4.4~4.7 (2H, m, —CH—CO—×2), 5.11 (2H, s, —CH$_2$Ph), 5.0~5.3 (1H, —NH—), 5.6~5.8 (1H, —NH—), 7.29 (5H, s, —CH$_2$Ph).

12-(3) Preparation of Z-(2S,3R)-AHMHA-Val-Val-Pro(OBzl)

By the same procedure as specified in Example 1-(3), 1.16 g of Boc-Val-Val-Pro(OBzl) was treated with trifluoroacetic acid and 717 mg of Val-Val-Pro(OBzl) thus formed was subjected to condensation with 525 mg of Z-(2S,3R)-AHMHA to give 568 mg of the title compound.

RF: 0.64 (benzene/acetone=4/1, a silica gel plate as described above).

m.p.: 63.0° C.

[α]$_D^{21}$: −79.4° (c=1.0, CH$_3$COOH).

n.m.r. δppm (CDCl$_3$): 0.8~1.1 (18H, m, —CH(CH$_3$)$_2$×3), 1.3~2.4 (9H, m, —CH(CH$_3$)$_2$×3, —CH$_2$—CH(CH$_3$)$_2$, —(CH$_2$)$_2$—), 3.0~4.8

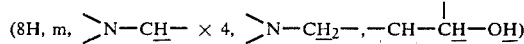

5.02 and 5.10 (4H, each s, —CH$_2$—Ph.×2), 5.3~6.1 (2H, —NH—×2), 7.25 (10H, s, —CH$_2$P$\underline{h}$×2), 7.3~7.6 (1H, —NH—).

12-(4) Preparation of (2S,3R)-AHMHA-Val-Val-Pro

Z-(2S,3R)-AHMHA-Val-Val-Pro(OBzl)(204 mg) was dissolved in 30 ml of a solvent mixture of methanol, acetic acid and water (4/2/1) and, under the same operational conditions as presented in Example 1-(4), submitted to catalytic reduction with 50 mg of 10% palladium-charcoal catalyst to give 128 mg of the desired compound.

Rf: 0.61 (butanol/acetic acid/water=4/1/2, a silica gel plate).

m.p.: 176.0° C.

[α]$_D^{21}$: −88.6° (c=0.5, CH$_3$COOH).

Elemental analysis(for C$_{22}$H$_{40}$N$_4$O$_6$): Found: C, 58.04%; H, 8.95%; N, 12.05%. Calculated: C, 57.87%; H, 8.83%; N, 12.27%.

Example 13

Synthesis of (2S,3R)-AHMHA-Val-Val-Phe 13-(1) Synthesis of Boc-Val-Phe(OBzl)

Phe(OBzl).TosOH(427 mg) and 110 μl of N-methylmorpholine (abbreviated NMM herafter) were dissolved in 20 ml of THF and then, under the same reaction conditions as detailed in Example 1-(1), treated with 217 mg of Boc-Val, 148 mg of HOBt and 227 mg of DCCD to give 430 mg of the title compound.

Rf: 0.93 (benzene/acetone=4/1, a silica gel plate as described above).

n.m.r. δppm (CDCl$_3$): 0.86, 0.89 (6H, each d, —CH(C$\underline{H}_3$)$_2$), 1.43 (9H, s, —O—C—(CH$_3$)$_3$), 1.80~2.40 (1H, m, —C$\underline{H}$(CH$_3$)$_2$), 3.10 (2H, d, $>$CH—C$\underline{H}_2$—Ph)

3.70 ~ 4.10 (2H, m, —NH—C$\underline{H}$ . CO— × 2)

5.12 (2H, s, —O—CH$_2$—Ph), 6.90~7.50 (5H, m, —CH$_2$P$\underline{h}$), 7.32 (5H, s, —OCH$_2$P$\underline{h}$).

13-(2) Synthesis of Boc-Val-Val-Phe(OBzl)

By the same method as explained in Example 1-(2), 530 mg of Boc-Val-Phe(OBzl) was treated with trifluoroacetic acid to provide 484 mg of Val-Phe(OBzl), with which 296 mg of Boc-Val was condensed to yield 469 mg of the title compound.

Rf: 0.62 (benzene/acetone=4/1, a silica gel plate as described above).

m.p.: 114.0° C.

n.m.r. δppm (CDCl$_3$): 0.90 (12H, broad d, —CH(C$\underline{H}_3$)$_2$×2), 1.42 (9H, s, —C(CH$_3$)$_3$), 3.17 (2H, d, —C—C$\underline{H}_2$Ph), 5.09 (2H, s, —O—CH$_2$Ph), 7.0~7.6 (10H, m+s, —P$\underline{h}$×2).

13-(3) Synthesis of Z-(2S,3R)-AHMHA-Val-Val-Phe(OBzl)

According to the same method as described in Example 1-(3), the treatment of 342 mg of Boc-Val-Val-Phe(OBzl) with trifluoroacetic acid resulted in 270 mg of Val-Val-Phe(OBzl), from which 343 mg of the title compound was obtained by condensation with 163 mg of Z-(2S,3R)-AHMHA.

Rf: 0.76 (benzene/acetone=4/1, a silica gel plate as described above).

m.p.: 61.5° C.

[α]$_D^{21}$: −80.6° (c=0.5, CH$_3$COOH).

n.m.r. δppm (CDCl$_3$): 0.8~1.0 (18H, m, —CH(C$\underline{H}_3$)$_2$×3), 3.05

(2H, d, J = 7Hz, $>$CH—C$\underline{H}_2$—Ph)

5.03 (2H, s, —O—CH$_2$—Ph), 5.08 (2H, s, —O—C$\underline{H}_2$—Ph), 6.8~7.4 (15H, —CH$_2$P$\underline{h}$×3).

13-(4) Synthesis of (2S,3R)-AHMHA-Val-VAl-Phe

The same treatment as specified in Example 1-(4) was repeated to yield 213 mg of the desired derivative, except that 320 mg of Z-(2S,3R)-AHMHA-Val-Val-Phe(OBzl) and 80 mg of 10% palladium-charcoal catalyst was suspended in 16 ml of a solvent mixture of methanol, acetic acid and water (4/2/1).

Rf: 0.77 (butanol/acetic acid/water=4/1/2, a silica gel plate as described above).

m.p.: 164.7° C.

[α]$_D^{21}$: −18.8° (c=0.5, CH$_3$COOH).

Elemental analysis (for C$_{26}$H$_{42}$N$_4$O$_6$): Found: C, 61.38%; H, 8.61%; N, 10.84%. Calculated: C, 61.63%; H, 8.36%; N, 11.06%.

Example 14

Synthesis of (2S,3R)-AHMHA-Val-Val-Val 14-(1) Preparation of Boc-Val-Val-Val(OBzl)

Boc-Val-Val (395 mg) obtained by the same method as specified in Example 12-(1) and 474 mg of Val-OBzl.TosOH were subjected to condensation and processed by the same procedure as explained in Example 1-(2) to provide 605 mg of the desired derivative.

n.m.r. δppm (CDCl$_3$): 0.7~1.0 (18H, —CH(C$\underline{H}_3$)$_2$×3), 1.4 (9H, s, —C(CH$_3$)$_3$), 1.8~2.3 (3H, —C$\underline{H}$(CH$_3$)$_2$×3), 3.8~4.1 (1H, —NH—C$\underline{H}$—CO—), 4.2~4.7 (2H, —NH—C$\underline{H}$—CO—×2), 5.05~5.15 (2H, —OCH$_2$Ph), 5.4~5.7 (1H, —N$\underline{H}$—), 6.7~7.2 (2H, —N$\underline{H}$—×2), 7.28 (5H, s, —O—CH$_2$P$\underline{h}$).

14-(2) Preparation of Z-(2S,3R)-AHMHA-Val-Val-Val(OBzl)

The treatment of 278 mg of Boc-Val-Val-Val(OBzl) with trifluoroacetic acid under the same operational conditions as described in Example 1-(3) produced a free amine which, on condensation with 129 mg of Z-(2S,3R)-AHMHA, resulted in 250 mg of crystals of the title compound.

n.m.r δppm (CDCl$_3$): 0.7~1.05 (24H, —CH(C$\underline{H}_3$)$_2$×4), 5.0~5.18 (4H, —OCH$_2$Ph×2), 7.28 (10H, s, —OCH$_2$P$\underline{h}$×2). (Only characteristic signals are listed).

14-(3) Preparation of (2S,3R)-AHMHA-Val-Val-Val

Z-(2S,3R)-AHMHA-Val-Val-Val(OBzl) (246 mg) was dissolved in a mixed solvent of methanol, acetic acid and water (8/2/1) (15 ml) and then subjected to catalytic reduction in the presence of 10%-palladium-charcoal catalyst (50 mg) under the same operational conditions as detailed in Example 1-(4) to yield 114.8 mg of the title compound.

Rf: 0.77(butanol/acetic acid/water=4/1/2, a silica gel plate as described above).

m.p.: 79.5° C.

[α]$_D^{21}$: −62.6° (c=0.5, CH$_3$COOH).

Elemental analysis (for C$_{22}$H$_{42}$N$_4$O$_6$): Found: C, 57.37%; H, 9.28%; N, 11.94%. Calculated: C, 57.62%; H, 9.23%; N, 12.22%.

Example 15

Synthesis of (2S,3R)-AHMHA-Val-Val-Lys 15-(1) Synthesis of Boc-Val-Lys(Z)-OBzl

Using 217.3 mg of Boc-Val and 407 mg of Lys(Z)-OBzl.Hcl, the same reaction and treatment as explained in Example 1-(1) was performed to give 613 mg of the title derivative.

n.m.r. δppm (CDCl$_3$): 0.82, 0.95 (6H, each d, J=4 Hz, —CH(C$\underline{H}_3$)$_2$), 1.40 (9H, s, —C(CH$_3$)$_3$), 1.1~2.1 (7H, m, —(CH$_2$)$_3$—, —C$\underline{H}$(CH$_3$)$_2$), 2.9~3.2 (2H, m, —NH—C$\underline{H}_2$—), 3.7~4.5 (2H, m, —NH—C$\underline{H}$—CO—), 5.08, 5.15 (4H, each s, —C$\underline{H}_2$Ph×2), 6.5~7.0 (2H, m, —NH—×2), 7.35 (10H, s, —CH$_2$P$\underline{h}$×2).

15-(2) Synthesis of Boc-Val-Val-Lys(Z)-OBzl

By the same procedure as detailed in Example 1-(2), 362 mg of Boc-Val-Lys(Z)-OBzl was treated with trifluoroacetic acid to give a free amine which was condensed with 122 mg of Boc-Val for production of 286 mg of the aimed compound.

n.m.r. δppm (CDCl$_3$—$_{CD_3}$OD): 0.9 (12H, d, J=6 Hz, —CH(C$\underline{H}_3$)$_2$×2), 1.45 (9H, s, —C(CH$_3$)$_2$), 1.0~2.4 (8H, —C$\underline{H}$(CH$_3$)$_2$×2, —(CH$_2$)$_3$—), 2.9~3.2 (2H, —C$\underline{H}_2$—NHZ), 3.8~4.9 (3H, —NH—C$\underline{H}$—CO—×3), 5.1 and 5.15 (4H, each s, —C$\underline{H}_2$Ph×2), 7.32 (10H, s, —CH$_2$P$\underline{h}$×2).

15-(3) Synthesis of Z-(2S,3R)-AHMHA-Val-Val-Lys(Z)-OBzl

Free amine which was derived from 286 mg of Boc-Val-Val-Lys(Z)-OBzl by treatment with trifluoroacetic acid under the same reaction conditions as detailed in Example 1-(3) was submitted to condensation with 124 mg of Z-(2S,3R)-AHMHA to yield 177 mg of the desired compound.

n.m.r. δppm (CDCl$_3$): 0.87 (18H, d-like, —CH(C$\underline{H}_3$)$_2$×3), 5.0, 5.05 and 5.12 (6H, each s, —C$\underline{H}_2$Ph×3), 7.30 (15H, s, —CH$_2$P$\underline{h}$×3).

15-(4) Synthesis of (2S,3R)-AHMHA-Val-Val-Lys

Solution of 175 mg of Z-(2S,3R)-AHMHA-Val-Val-Lys(Z)-OBzl in 30 ml of a mixed solvent of methanol, acetic acid and water (4/2/1) was hydrogenolysed under the same reaction conditions as defined in Example 2-(4) to yield 77.1 mg of the title compound.

Rf: 0.27 (butanol/acetic acid/water=4/1/2, a silica gel plate as described above).

m.p.: 224.2° C.

[α]$_D^{21}$: −51.2° (c=0.5, CH$_3$COOH).

Elemental analysis (for C$_{23}$H$_{45}$N$_5$O$_6$): Found: C, 56.41%; H, 9.56%; N, 14.11%. Calculated: C, 56.65%; H, 9.30%; N, 14.36%.

Example 16

Synthesis of (2S,3R)-AHMHA-Val-Val-Arg 16-(1) Preparation of Boc-Val-Arg[NO$_2$]-OBzl Utilizing 0.439 g of Boc-Val and 1.307 g of Arg-[NO$_2$]-OBzl.2TosOH, the same reaction and treatment as described in Example 1-(1) was repeated to give 0.968 g of the desired product.

n.m.r. δppm (CDCl$_3$): 0.95 (6H, d, J=6 Hz, —CH(C$\underline{H}_3$)$_2$), 1.4 (9H, s, —C(CH$_3$)$_3$), 1.3~2.2 (5H, —COCH(C$\underline{H}_2$)$_2$—, —C$\underline{H}$—(CH$_3$)$_2$)

3.0~3.7 (2H, —C$\underline{H}_2$—NH—C=N—)

3.7~4.2 (1H, —NH—C$\underline{H}$—CO—)

4.4~4.8 (1H, —NH—C$\underline{H}$—CO—)

5.17 (2H, s, —OCH$_2$Ph), 5.1~5.4 (1H, —NH—), 7.0~7.2 (1H, —N$\underline{H}$—), 7.34 (5H, s, —OCH$_2$P$\underline{h}$), 7.3~7.9 (3H, —NH—×3).

16-(2) Preparation of Boc-Val-Val-Arg[NO$_2$]-BOzl

The same trifluoroacetic acid treatment of 0.960 g of Boc-Val-Arg[NO$_2$]-OBzl as specified in Example 1-(2) led to the formation of a free amine which was subjected to condensation with 0.304 g of Boc-Val to provide 0.605 g of the desired compound.

n.m.r. δppm (CDCl$_3$): 0.9 (12H, d-like, —CH(C$\underline{H}_3$)$_2$×2), 1.4 (9H, s, —C(C$\underline{H}_3$)$_3$), 5.15 (2H, s, —O—CH$_2$Ph), 7.32 (5H, s, —O—CH$_2$P$\underline{h}$). (Only characteristic signals are listed).

16-(3) Preparation of Z-(2S,3R)-AHMHA-Val-Val-Arg[NO$_2$]-OBzl

Free amine that was obtained from 143 mg of Boc-Val-Val-Arg[NO$_2$]-OBzl by the same trifluoroacetic acid treatment as explained in Example 1-(3) was subjected to condensation with 81.6 mg of Z-(2S,3R)-AHMHA to give 152 mg of the title compound.

n.m.r. δppm (CDCl$_3$—CD$_3$COCD$_3$—CD$_3$OD): 0.8~1.05 (12H, broad d, —CH(C$\underline{H}_3$)$_2$×2), 5.02 (2H, s, —OCH$_2$Ph), 5.16 (2H, s, —OCH$_2$Ph), 7.35 (10H, s, —CH$_2$P$\underline{h}$×2). (Only characteristic signals are listed).

16-(4) Preparation of (2S,3R)-AHMHA-Val-Val-Arg

Solution of 114 mg of Z-(2S,3R)-AHMHA-Val-Val-Arg[NO$_2$]-OBzl in 30 ml of a solvent mixture of methanol, acetic acid and water (4/2/1) was hydrogenolysed under the same reaction conditions as detailed in Example 1-(4) to provide 48.7 mg of the title compound.

Rf: 0.41 (butanol/acetic acid/water=4/1/2, a silica gel plate as described above).

m.p.: 97.5° C.

[α]$_D^{21}$: −38.6° (c=0.5, CH$_3$COOH).

Elemental analysis (for C$_{23}$H$_{45}$N$_7$O$_6$): Found: C, 53.44%; H, 9.08%; N, 18.75%. Calculated: C, 53.57%; H, 8.80%; N, 19.02%.

We claim:

1. Tetrapeptide derivatives of the formula (I):

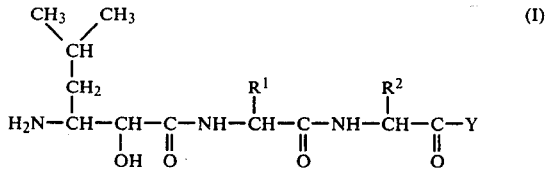

wherein R$^1$ and R$^2$ are methyl, 1-methylethyl, 2-methylpropyl, 1-hydroxyethyl, 2-carboxyethyl or 4-aminobutyl and Y is

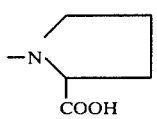 or 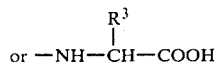 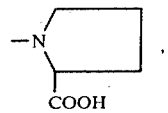

wherein R³ is methyl, 1-methylethyl, 2-methylpropyl, 1-methylpropyl, hydroxymethyl, 1-hydroxyethyl, carboxymethyl, 2-carboxyethyl, 4-aminobutyl, 3-guanidinopropyl, benzyl or p-hydroxybenzyl excluding the compounds in which R¹ and R² are each 1-methylethyl and also R³ is carboxymethyl or 2-carboxymethyl, the first and leftmost β-amino acid moiety in said tetrapeptide derivatives having the (2S,3R)-configuration and a primary amino group and the second, third and fourth α-amino acid moieties in said tetrapeptide derivatives having the L-configuration.

2. A compound of claim 1 in which R¹ is 1-methylethyl and R² is not 1-methylethyl.

3. A compound of claim 2 in which R² is 4-aminobutyl, 1-hydroxyethyl, 2-methylpropyl or 2-carboxyethyl.

4. A compound of claim 3 in which R³ is carboxymethyl.

5. A compound of claim 1 in which R² is 1-methylethyl and R¹ is not 1-methylethyl.

6. A compound of claim 5 in which R¹ is 4-aminobutyl, 1-hydroxyethyl, 2-methylpropyl or 2-carboxyethyl.

7. A compound of claim 6 in which R³ is carboxymethyl.

8. A compound of claim 1 in which both R¹ and R² are 1-methylethyl and R³ is neither carboxymethyl nor 2-carboxyethyl.

9. A compound of claim 8 in which R³ is 1-hydroxyethyl, benzyl, 1-methylethyl, 4-aminobutyl or 3-guanidinopropyl.

10. (2S,3R)-3-Amino-2-hydroxy-5-methyl-hexanoyl-Val-Lys-Asp.

11. (2S,3R)-3-Amino-2-hydroxy-5-methyl-hexanoyl-Val-Thr-Asp.

12. (2S,3R)-3-Amino-2-hydroxy-5-methyl-hexanoyl-Val-Leu-Asp.

13. (2S,3R)-3-Amino-2-hydroxy-5-methyl-hexanoyl-Val-Glu-Asp.

14. (2S,3R)-3-Amino-2-hydroxy-5-methyl-hexanoyl-Thr-Val-Asp.

15. (2S,3R)-3-Amino-2-hydroxy-5-methyl-hexanoyl-Leu-Val-Asp.

16. (2S,3R)-3-Amino-2-hydroxy-5-methyl-hexanoyl-Lys-Val-Asp.

17. (2S,3R)-3-Amino-2-hydroxy-5-methyl-hexanoyl-Glu-Val-Asp.

18. (2S,3R)-3-Amino-2-hydroxy-5-methyl-hexanoyl-Val-Thr-Phe.

19. (2S,3R)-3-Amino-2-hydroxy-5-methyl-hexanoyl-Lys-Val-Val.

20. (2S,3R)-3-Amino-2-hydroxy-5-methyl-hexanoyl-Val-Val-Thr.

21. (2S,3R)-3-Amino-2-hydroxy-5-methyl-hexanoyl-Val-Val-Pro.

22. (2S,3R)-3-Amino-2-hydroxy-5-methyl-hexanoyl-Val-Val-Phe.

23. (2S,3R)-3-Amino-2-hydroxy-5-methyl-hexanoyl-Val-Val-Val.

24. (2S,3R)-3-Amino-2-hydroxy-5-methyl-hexanoyl-Val-Val-Lys.

25. (2S,3R)-3-Amino-2-hydroxy-5-methyl-hexanoyl-Val-Val-Arg.

* * * * *